US 007863416B2

(12) United States Patent
Judd

(10) Patent No.: US 7,863,416 B2
(45) Date of Patent: *Jan. 4, 2011

(54) NOCICEPTIN-BASED ANALGESICS

(75) Inventor: Amrit K. Judd, North Logan, UT (US)

(73) Assignee: Synvax, Inc., North Logan, UT (US)

( * ) Notice: Subject to any disclaimer, the term of this patent is extended or adjusted under 35 U.S.C. 154(b) by 865 days.

This patent is subject to a terminal disclaimer.

(21) Appl. No.: 11/740,120

(22) Filed: Apr. 25, 2007

(65) Prior Publication Data

US 2008/0221304 A1 Sep. 11, 2008

Related U.S. Application Data

(63) Continuation of application No. 11/402,083, filed on Apr. 11, 2006, now abandoned, which is a continuation of application No. 10/268,020, filed on Oct. 9, 2002, now Pat. No. 7,049,287.

(60) Provisional application No. 60/327,888, filed on Oct. 9, 2001.

(51) Int. Cl.
*C07K 7/06* (2006.01)
(52) U.S. Cl. .................................. 530/329
(58) Field of Classification Search .............. None
See application file for complete search history.

(56) References Cited

U.S. PATENT DOCUMENTS

| 5,821,219 | A | 10/1998 | Grandy et al. | |
| 6,011,006 | A | 1/2000 | Thomsen et al. | |
| 7,049,287 | B2 * | 5/2006 | Judd | 514/7 |
| 7,244,701 | B2 * | 7/2007 | Larsen et al. | 514/2 |
| 7,550,425 | B2 * | 6/2009 | Larsen et al. | 514/2 |
| 2001/0011092 | A1 | 8/2001 | Tulshian et al. | |

FOREIGN PATENT DOCUMENTS

| EP | 1072263 | 1/2001 |
| WO | WO 99/44627 | 9/1999 |
| WO | WO 01/98324 | 12/2001 |

OTHER PUBLICATIONS

Khroyan, Taline V., et al., "Anti-Nociceptive and Anti-Allodynic Effects of a High Affinity NOP Hexapepetide [Ac-RY(3-C1)YRWR-NH2] (Syn 1020) in Rodents," ScienceDirect, Jan. 17, 2007, pp. 29-35.
Judd, A. K., et al., "Structure-Activity Studies on High Affinity NOP-Active Hexapeptides," J. Peptide Res., 2004, 64, pp. 87-94.
Judd, A.K., et al., "N-Terminal Modifications Leading to Peptide ORL1 Partial Agonists and Antagonists," J. Peptide Res., 2003, 62, pp. 191-198.
Encyclopedia Britannica, http://www.search.eb.com/eb/article?tocid=233942, Nov. 8, 2004.
Wikipedia, http://en.wikipedia.org/wiki/analgesic, Oct. 6, 2004.
Calo, Girolamo, et al., "Pharmacological Profile of Nociceptin/Orphanin FQ Receptors," Clinical and Experimental Pharmacology and Physiology, 29, 2002, 223-228.
Thomsen, Christian, et al., "[3H]ac-RYYRWK-NH2, a Novel Specific Radioligand for the Nociceptin/Orphanin FQ Receptor," Naunyn-Schmiedeberg's Arch Pharmacol (2000), 362:538-545.
Corbett et al., "Characterization of the ORL1 Receptor on Adrenergic Nerves in the Rat Anococcygeus Muscle," British Journal of Pharmacology, pp. 349-355, 2000.
Minks, Caroline, et al., "Towards New Protein Engineering: In Vivo Building and Folding of Protein Shuttles for Drug Delivery and Targeting by the Selective Pressure Incorporation (SPI) Method," Tetrahedron, Elsevier Science Ltd., (2000), 9431-9442.
Kawamoto, Hiroshi, et al., "Discovery of the First Potent and Selective Small Molecule Opioid Receptor-like (ORL1) Antagonist: 1-[(3R,4R)-1-Cyclooctylmethyl-3-hydroxymethyl-4-piperodyl]-3-ethyl-1,3-dihydro-2H-benzimidazol-2-one (J-113397)," Journal of Medicinal Chemistry, vol. 42, No. 25, Dec. 16, 1999, pp. 1-3.
Dooley et al., "113 Potent Orphanin FQ Receptor Ligands Identified Using Combinatorial Libraries," The European Peptide Society, pp. 343-344, 1998.
Dooley, Colette T., et al., "Binding and In Vitro Activities of Peptides with High Affinity for the Nociceptin/Orphanin FQ Receptor, ORL1," The Journal of Pharmacology and Experimental Therapeutics, vol. 283, No. 2, pp. 735-741, 1997.
On-line Medical Dictionary, Nov. 18, 1997, http://cancerweb.ncl.ac.uk./cgi-bin.omd?modify.
Khroyan, T.V., et al., "High Affinity Hexapeptides for ORL1 Receptors: In Vitro Activity and In Vivo Nociceptive Effects," No. 124.
J. Rudinger, Characteristics of the Amino Acids as Components of a Peptide Hormone Sequence, Peptide Hormones, University Park Press, Jun. 1976, pp. 1-7

* cited by examiner

*Primary Examiner*—Andrew D Kosar
(74) *Attorney, Agent, or Firm*—Craig Metcalf; Kirton & McConkie

(57) ABSTRACT

The invention relates to a family of hexapeptide compounds exhibiting activity with regard to the ORL-1 receptor. The compounds share a general formula of Arg-Tyr-Tyr-Arg-Trp-Arg, and may be constructed having modifications or substitutions at any position, and may include modifications of the amino- and carboxy-termini of the hexapeptide. These compounds include agents exhibiting agonist activity and antagonist activity when exposed to the human ORL-1 receptor. As such, the hexapeptides may be useful as analgesics, anxiolytics, diuretics, and anti-cancer agents.

19 Claims, 27 Drawing Sheets

IV-16-C

IV-17-C

VII-1-A

VII-2-A

VII-3-A

VII-4-B

VII-7-B

VII-9-A

VII-11-B

VII-13-B

VII-15-B

VII-17-B

VII-19-B

VII-21-C

VII-23-B

VII-25

VII-27-B

VII-29-B

VII-31-B

VII-33-B

VII-35-C

VII-37-B

VII-39-D

VII-41

VII-43-C

VII-1-A

VII-2-A

VII-3-A

VII-4-B

VII-7-B

VII-9-A

VII-11-B

VII-13-B

VII-15-B

VII-17-B

VII-19-B

VII-21-C

VII-23-B

VII-25

VII-27-B

VII-29-B

VII-31-B

VII-33-B

VII-35-C

VII-37-B

VII-39-D

VII-41

VII-43-C

MW: 1112.32
Formula: C53H79N18O9
Name: VII-1-A

MW: 1114.34
Formula: C53H81N18O9
Name: VII-2-A

MW: 1086.28
Formula: C51H77N18O9
Name: VII-3-A

MW: 1140.38
Formula: C55H83N18O9
Name: VII-4-B

MW: 1070.28
Formula: C52H77N16O9
Name: VII-7-B

MW: 1013.19
Formula: C48H70N17O8
Name: VII-9-A

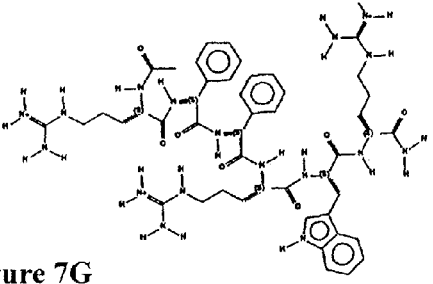

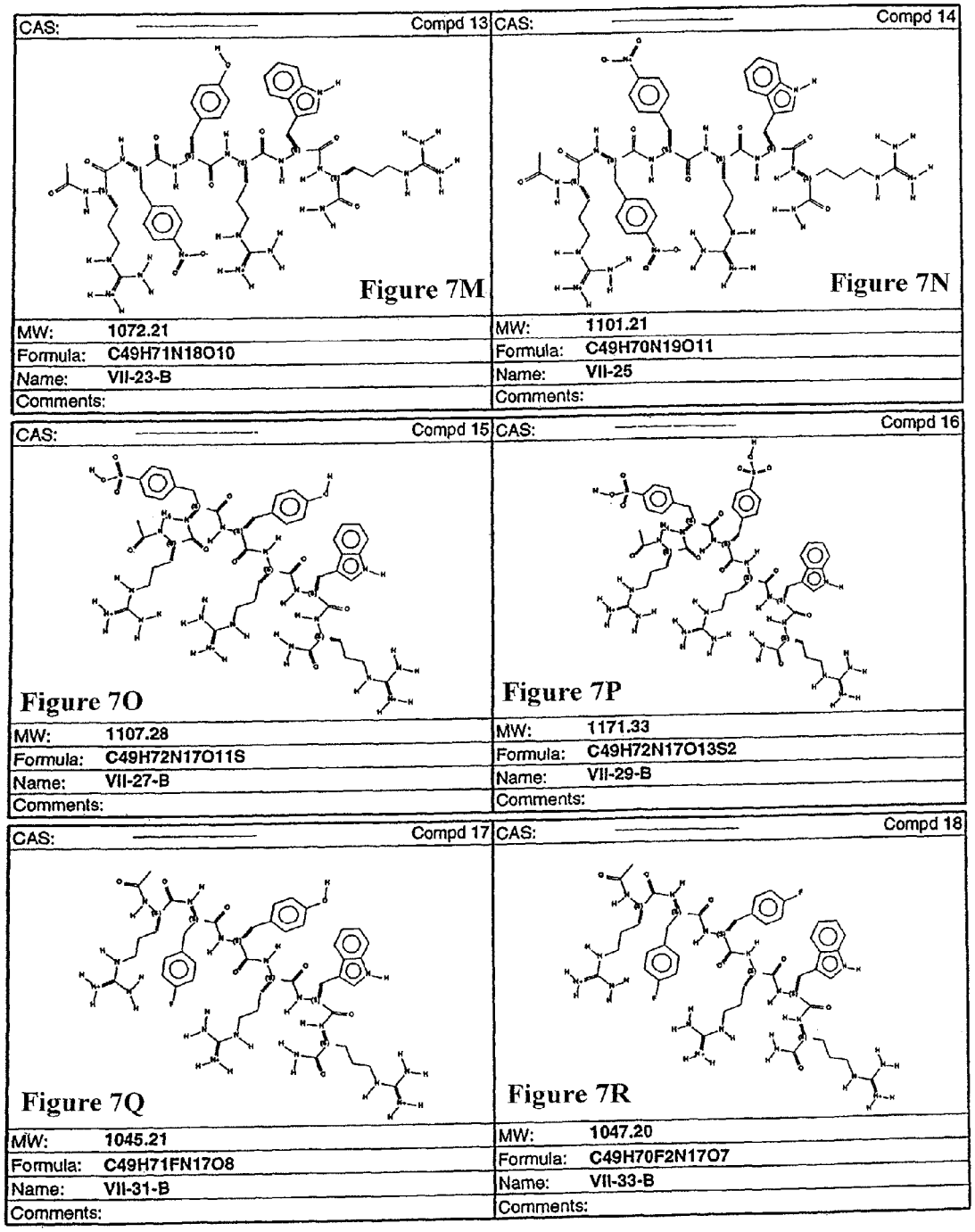

| | |
|---|---|
| CAS: — Compd 19<br>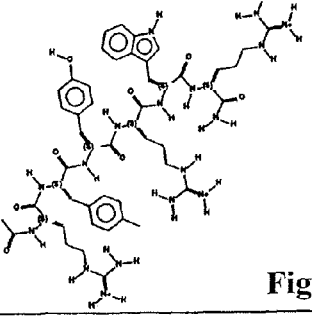<br>Figure 7S<br>MW: 1041.24<br>Formula: C50H74N17O8<br>Name: VII-35-C<br>Comments: | CAS: — Compd 20<br>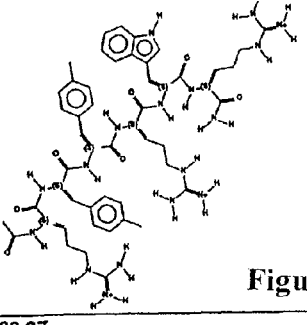<br>Figure 7T<br>MW: 1039.27<br>Formula: C51H76N17O7<br>Name: VII-37-B<br>Comments: |
| CAS: — Compd 21<br>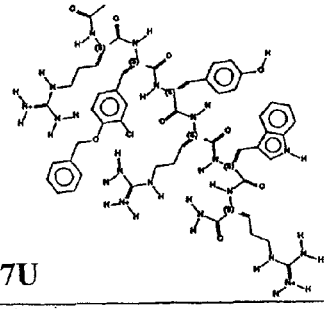<br>Figure 7U<br>MW: 1167.79<br>Formula: C56H77ClN17O9<br>Name: VII-39-D<br>Comments: | CAS: — Compd 22<br>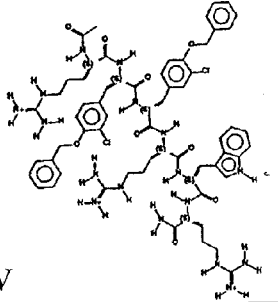<br>Figure 7V<br>MW: 1292.36<br>Formula: C63H82Cl2N17O9<br>Name: VII-41<br>Comments: |
| CAS: — Compd 23<br>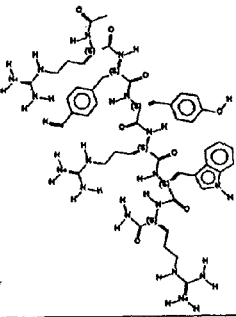<br>Figure 7W<br>MW: 1052.23<br>Formula: C50H71N18O8<br>Name: VII-43-C<br>Comments: | CAS:<br><br>MW:<br>Formula:<br>Name:<br>Comments: |

```
                            SEQUENCE LISTING

<160> NUMBER OF SEQ ID NOS: 57

<210> SEQ ID NO 1
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-15-B Hexapeptide
<220> FEATURE:
<221> NAME/KEY: MISC_FEATURE
<222> LOCATION: (2)..(2)
<223> OTHER INFORMATION: X is 4-Methyl Phenylalanine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 1

Arg Xaa Tyr Arg Trp Arg
1               5

<210> SEQ ID NO 2
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-19-B Hexapeptide
<220> FEATURE:
<221> NAME/KEY: MISC_FEATURE
<222> LOCATION: (2)..(2)
<223> OTHER INFORMATION: X is 4-COOH Phenylalanine
<220> FEATURE:
<221> NAME/KEY: MISC_FEATURE
<222> LOCATION: (1)..(1)
<223> OTHER INFORMATION: N terminal modification to include acetyl.
<220> FEATURE:
<221> NAME/KEY: MISC_FEATURE
<222> LOCATION: (6)..(6)
<223> OTHER INFORMATION: C terminal modification to include NH2.
```

```
<400> SEQUENCE: 2

Arg Xaa Tyr Arg Trp Arg
1               5

<210> SEQ ID NO 3
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-23-B Hexapeptide
<220> FEATURE:
<221> NAME/KEY: MISC_FEATURE
<222> LOCATION: (2)..(2)
<223> OTHER INFORMATION: X is 4-NO2 Phenylalanine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 3

Arg Xaa Tyr Arg Trp Arg
1               5

<210> SEQ ID NO 4
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-31-B Hexapeptide
<220> FEATURE:
<221> NAME/KEY: MISC_FEATURE
<222> LOCATION: (2)..(2)
<223> OTHER INFORMATION: X is 4-Fluoro Phenylalanine
<220> FEATURE:
<221> NAME/KEY: MISC_FEATURE
<222> LOCATION: (1)..(1)
<223> OTHER INFORMATION: N terminal is modified to include acetyl.
<220> FEATURE:
<221> NAME/KEY: MISC_FEATURE
<222> LOCATION: (6)..(6)
<223> OTHER INFORMATION: C terminal is modified to include NH2.

<400> SEQUENCE: 4

Arg Xaa Tyr Arg Trp Arg
1               5

<210> SEQ ID NO 5
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-35-C Hexapeptide
<220> FEATURE:
<221> NAME/KEY: MISC_FEATURE
<222> LOCATION: (2)..(2)
<223> OTHER INFORMATION: X is 4-Methyl Tyrosine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
```

```
<222> LOCATION: (6)..(6)
<223> OTHER INFORMATION: C terminal modified to include NH2.

<400> SEQUENCE: 5

Arg Xaa Tyr Arg Trp Arg
1               5

<210> SEQ ID NO 6
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-43-C Hexapeptide
<220> FEATURE:
<221> NAME/KEY: MISC_FEATURE
<222> LOCATION: (2)..(2)
<223> OTHER INFORMATION: X is 4-CN Phenylalanine
<220> FEATURE:
<221> NAME/KEY: MISC_FEATURE
<222> LOCATION: (1)..(1)
<223> OTHER INFORMATION: N terminal modied to include acetyl.
<220> FEATURE:
<221> NAME/KEY: MISC_FEATURE
<222> LOCATION: (6)..(6)
<223> OTHER INFORMATION: C terminal modied to include NH2.

<400> SEQUENCE: 6

Arg Xaa Tyr Arg Trp Arg
1               5

<210> SEQ ID NO 7
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-39-D Hexapeptide
<220> FEATURE:
<221> NAME/KEY: MISC_FEATURE
<222> LOCATION: (2)..(2)
<223> OTHER INFORMATION: X is Benzyl, 3-Cl Tyrosine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 7

Arg Xaa Tyr Arg Trp Arg
1               5

<210> SEQ ID NO 8
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-51-A Hexapeptide
<220> FEATURE:
<221> NAME/KEY: MISC_FEATURE
<222> LOCATION: (5)..(5)
<223> OTHER INFORMATION: X is 5-CN Tryptophan
<220> FEATURE:
<221> NAME/KEY: MISC_FEATURE
<222> LOCATION: (1)..(1)
<223> OTHER INFORMATION: N terminal modified to include acetyl.
```

```
<220> FEATURE:
<221> NAME/KEY: MISC_FEATURE
<222> LOCATION: (6)..(6)
<223> OTHER INFORMATION: C terminal modified to include NH2.

<400> SEQUENCE: 8

Arg Tyr Tyr Arg Xaa Arg
1               5

<210> SEQ ID NO 9
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-53-B Hexapeptide
<220> FEATURE:
<221> NAME/KEY: MISC_FEATURE
<222> LOCATION: (1)..(1)
<223> OTHER INFORMATION: X is epsilon-Aminocaproyl
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 9

Xaa Tyr Tyr Arg Trp Arg
1               5

<210> SEQ ID NO 10
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-55-A Hexapeptide
<220> FEATURE:
<221> NAME/KEY: MISC_FEATURE
<222> LOCATION: (4)..(4)
<223> OTHER INFORMATION: X is epsilon-Aminocaproyl
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 10

Arg Tyr Tyr Xaa Trp Arg
1               5

<210> SEQ ID NO 11
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-57-C Hexapeptide
<220> FEATURE:
<221> NAME/KEY: MISC_FEATURE
<222> LOCATION: (6)..(6)
<223> OTHER INFORMATION: X is epsilon-Aminocaproyl
<220> FEATURE:
<221> NAME/KEY: MISC_FEATURE
```

<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 11

Arg Tyr Tyr Arg Trp Xaa
1               5

<210> SEQ ID NO 12
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-61-B Hexapeptide
<220> FEATURE:
<221> NAME/KEY: MISC_FEATURE
<222> LOCATION: (3)..(3)
<223> OTHER INFORMATION: X is 4-Fluoro Phenylalanine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 12

Arg Tyr Xaa Arg Trp Arg
1               5

<210> SEQ ID NO 13
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-63-B Hexapeptide
<220> FEATURE:
<221> NAME/KEY: MISC_FEATURE
<222> LOCATION: (3)..(3)
<223> OTHER INFORMATION: X is 4-NO2 Phenylalanine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 13

Arg Tyr Xaa Arg Trp Arg
1               5

<210> SEQ ID NO 14
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-65-F Hexapeptide
<220> FEATURE:
<221> NAME/KEY: MISC_FEATURE
<222> LOCATION: (1)..(1)
<223> OTHER INFORMATION: X is DAP

```
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 14

Xaa Tyr Tyr Arg Trp Arg
1               5

<210> SEQ ID NO 15
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-73-A Hexapeptide
<220> FEATURE:
<221> NAME/KEY: MISC_FEATURE
<222> LOCATION: (3)..(3)
<223> OTHER INFORMATION: X is 2, 6 dimethyl Tyrosine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 15

Arg Tyr Xaa Arg Trp Arg
1               5

<210> SEQ ID NO 16
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-77-A Hexapeptide
<220> FEATURE:
<221> NAME/KEY: MISC_FEATURE
<222> LOCATION: (3)..(3)
<223> OTHER INFORMATION: X is 4-NH-Ac Phenylalanine
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 16

Arg Tyr Xaa Arg Trp Arg
1               5

<210> SEQ ID NO 17
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: Second-position substitution.
<220> FEATURE:
<221> NAME/KEY: MISC_FEATURE
```

```
<222> LOCATION: (2)..(2)
<223> OTHER INFORMATION: X is selected from natural amino acids, D-amino
      acids, non-natural amino acids, and modified natural amino acids.

<400> SEQUENCE: 17

Arg Xaa Tyr Arg Trp Arg
1               5

<210> SEQ ID NO 18
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: 3-position substitution.
<220> FEATURE:
<221> NAME/KEY: MISC_FEATURE
<222> LOCATION: (3)..(3)
<223> OTHER INFORMATION: X is selected from natural amino acids, D-amino
      acids, non-natural amino acids, and modified natural amino acids.

<400> SEQUENCE: 18

Arg Tyr Xaa Arg Trp Arg
1               5

<210> SEQ ID NO 19
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: 1, 4, or 6 position substitution.
<220> FEATURE:
<221> NAME/KEY: MISC_FEATURE
<222> LOCATION: (1)..(1)
<223> OTHER INFORMATION: X is selected from natural amino acids, D-amino
      acids, non-natural amino acids, and modified natural amino acids.
<220> FEATURE:
<221> NAME/KEY: MISC_FEATURE
<222> LOCATION: (4)..(4)
<223> OTHER INFORMATION: X is selected from natural amino acids, D-amino
      acids, non-natural amino acids, and modified natural amino acids.
<220> FEATURE:
<221> NAME/KEY: MISC_FEATURE
<222> LOCATION: (6)..(6)
<223> OTHER INFORMATION: X is selected from natural amino acids, D-amino
      acids, non-natural amino acids, and modified natural amino acids.

<400> SEQUENCE: 19

Xaa Tyr Tyr Xaa Trp Xaa
1               5

<210> SEQ ID NO 20
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-71-B Hexapeptide
<220> FEATURE:
<221> NAME/KEY: MISC_FEATURE
<222> LOCATION: (3)..(3)
<223> OTHER INFORMATION: X is 2, 4 di-NO2 hPhenylalanine
<220> FEATURE:
<221> NAME/KEY: MISC_FEATURE
<222> LOCATION: (3)..(3)
<223> OTHER INFORMATION: hPhe is homophenylalanine

<400> SEQUENCE: 20
```

Arg Tyr Xaa Arg Trp Arg
1               5

<210> SEQ ID NO 21
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-75-B Hexapeptide
<220> FEATURE:
<221> NAME/KEY: MISC_FEATURE
<222> LOCATION: (3)..(3)
<223> OTHER INFORMATION: X is 4-CH2SO3H Phenylalanine

<400> SEQUENCE: 21

Arg Tyr Xaa Arg Trp Arg
1               5

<210> SEQ ID NO 22
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-79-A Hexapeptide
<220> FEATURE:
<221> NAME/KEY: MISC_FEATURE
<222> LOCATION: (3)..(3)
<223> OTHER INFORMATION: X is 4-CH2NH2 Phenylalanine

<400> SEQUENCE: 22

Arg Tyr Xaa Arg Trp Arg
1               5

<210> SEQ ID NO 23
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-87-B Hexapeptide
<220> FEATURE:
<221> NAME/KEY: MISC_FEATURE
<222> LOCATION: (2)..(2)
<223> OTHER INFORMATION: X is 3-Cl Tyrosine
<220> FEATURE:
<221> NAME/KEY: MISC_FEATURE
<222> LOCATION: (1)..(1)
<223> OTHER INFORMATION: N terminal may optionally be modified to
      include acetyl.
<220> FEATURE:
<221> NAME/KEY: MISC_FEATURE
<222> LOCATION: (6)..(6)
<223> OTHER INFORMATION: C terminal may optionally be modified to
      include NH2.

<400> SEQUENCE: 23

Arg Xaa Tyr Arg Trp Arg
1               5

<210> SEQ ID NO 24
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-16-C Hexapeptide

```
<220> FEATURE:
<221> NAME/KEY: MISC_FEATURE
<222> LOCATION: (1)..(1)
<223> OTHER INFORMATION: N-terminal modification to include a propionyl.
<220> FEATURE:
<221> NAME/KEY: MISC_FEATURE
<222> LOCATION: (6)..(6)
<223> OTHER INFORMATION: Carboxy-terminal modification to include NH2.

<400> SEQUENCE: 24

Arg Tyr Tyr Arg Trp Arg
1               5

<210> SEQ ID NO 25
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-17-C Hexapeptide
<220> FEATURE:
<221> NAME/KEY: MISC_FEATURE
<222> LOCATION: (1)..(1)
<223> OTHER INFORMATION: N-terminal modified to include hexanoyl.
<220> FEATURE:
<221> NAME/KEY: MISC_FEATURE
<222> LOCATION: (6)..(6)
<223> OTHER INFORMATION: Carboxy terminal modified to include NH2.

<400> SEQUENCE: 25

Arg Tyr Tyr Arg Trp Arg
1               5

<210> SEQ ID NO 26
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-7-B Hexapeptide
<220> FEATURE:
<221> NAME/KEY: MISC_FEATURE
<222> LOCATION: (1)..(1)
<223> OTHER INFORMATION: N-terminal is modified to include pentanoyl.
<220> FEATURE:
<221> NAME/KEY: MISC_FEATURE
<222> LOCATION: (6)..(6)
<223> OTHER INFORMATION: C-terminal is modified to include NH2.

<400> SEQUENCE: 26

Arg Tyr Tyr Arg Trp Arg
1               5

<210> SEQ ID NO 27
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: 5-position substitution.
<220> FEATURE:
<221> NAME/KEY: MISC_FEATURE
<222> LOCATION: (5)..(5)
<223> OTHER INFORMATION: X is selected from natural amino acids, D-amino
      acids, non-natural amino acids, and modified natural amino acids.

<400> SEQUENCE: 27

Arg Tyr Tyr Arg Xaa Arg
1               5
```

```
<210> SEQ ID NO 28
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-1-A Hexapeptide
<220> FEATURE:
<221> NAME/KEY: MISC_FEATURE
<222> LOCATION: (1)..(1)
<223> OTHER INFORMATION: N terminal modified to include nipacotyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 28

Arg Tyr Tyr Arg Trp Arg
1               5

<210> SEQ ID NO 29
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-2-A hexapeptide.
<220> FEATURE:
<221> NAME/KEY: MISC_FEATURE
<222> LOCATION: (1)..(1)
<223> OTHER INFORMATION: N terminal modified to include Beta-Nva.
<220> FEATURE:
<221> NAME/KEY: MISC_FEATURE
<222> LOCATION: (6)..(6)
<223> OTHER INFORMATION: C terminal modified to include NH2.

<400> SEQUENCE: 29

Arg Tyr Tyr Arg Trp Arg
1               5

<210> SEQ ID NO 30
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-3-A hexapeptide
<220> FEATURE:
<221> NAME/KEY: MISC_FEATURE
<222> LOCATION: (1)..(1)
<223> OTHER INFORMATION: N terminal modified to include
      Beta-aminoisobutryl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 30

Arg Tyr Tyr Arg Trp Arg
1               5

<210> SEQ ID NO 31
<211> LENGTH: 6
<212> TYPE: PRT
<213> ORGANISM: Artificial
<220> FEATURE:
<223> OTHER INFORMATION: Chemically Synthesized
<220> FEATURE:
```

```
<223> OTHER INFORMATION: VII-4-B hexapeptide
<220> FEATURE:
<221> NAME/KEY: MISC_FEATURE
<222> LOCATION: (1)..(1)
<223> OTHER INFORMATION: N terminal modified to include
      1-aminocyclohexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 31

Arg Tyr Tyr Arg Trp Arg
1               5

<210> SEQ ID NO 32
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-11-B hexapeptide.
<220> FEATURE:
<221> NAME/KEY: MISC_FEATURE
<222> LOCATION: (2)..(3)
<223> OTHER INFORMATION: X is Phg (phenylglycine).
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 32

Arg Xaa Xaa Arg Trp Arg
1               5

<210> SEQ ID NO 33
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-13-B hexapeptide.
<220> FEATURE:
<221> NAME/KEY: MISC_FEATURE
<222> LOCATION: (3)..(3)
<223> OTHER INFORMATION: X is Phg.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 33

Arg Tyr Xaa Arg Trp Arg
1               5

<210> SEQ ID NO 34
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-17-B hexapeptide.
```

```
<220> FEATURE:
<221> NAME/KEY: MISC_FEATURE
<222> LOCATION: (2)..(3)
<223> OTHER INFORMATION: X is 4-Me Phenylalanine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 34

Arg Xaa Xaa Arg Trp Arg
1               5

<210> SEQ ID NO 35
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-21-C hexapeptide.
<220> FEATURE:
<221> NAME/KEY: MISC_FEATURE
<222> LOCATION: (2)..(3)
<223> OTHER INFORMATION: X is 4-COOH Phenylalanine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 35

Arg Xaa Xaa Arg Trp Arg
1               5

<210> SEQ ID NO 36
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-27-B hexapeptide.
<220> FEATURE:
<221> NAME/KEY: MISC_FEATURE
<222> LOCATION: (2)..(2)
<223> OTHER INFORMATION: X is (4-SO3H) Phenylalanine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 36

Arg Xaa Tyr Arg Trp Arg
1               5

<210> SEQ ID NO 37
<211> LENGTH: 6
<212> TYPE: PRT
<213> ORGANISM: Artificial
<220> FEATURE:
<223> OTHER INFORMATION: Chemically Synthesized
```

```
<220> FEATURE:
<223> OTHER INFORMATION: VII-29-B hexapeptide.
<220> FEATURE:
<221> NAME/KEY: MISC_FEATURE
<222> LOCATION: (2)..(3)
<223> OTHER INFORMATION: X is (4-SO3H) Phenylalanine.
<220> FEATURE:
<221> NAME/KEY: MISC_FEATURE
<222> LOCATION: (1)..(1)
<223> OTHER INFORMATION: N terminal is modified to include acetyl.
<220> FEATURE:
<221> NAME/KEY: MISC_FEATURE
<222> LOCATION: (6)..(6)
<223> OTHER INFORMATION: C terminal is modified to include NH2.

<400> SEQUENCE: 37

Arg Xaa Xaa Arg Trp Arg
1               5

<210> SEQ ID NO 38
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-33-B hexapeptide.
<220> FEATURE:
<221> NAME/KEY: MISC_FEATURE
<222> LOCATION: (2)..(3)
<223> OTHER INFORMATION: X is 4-F Phenylalanine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 38

Arg Xaa Xaa Arg Trp Arg
1               5

<210> SEQ ID NO 39
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-37-B hexapeptide.
<220> FEATURE:
<221> NAME/KEY: MISC_FEATURE
<222> LOCATION: (2)..(3)
<223> OTHER INFORMATION: X is (4-Me) Tyrosine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 39

Arg Xaa Xaa Arg Trp Arg
1               5

<210> SEQ ID NO 40
<211> LENGTH: 6
<212> TYPE: PRT
<213> ORGANISM: Artificial
```

```
<220> FEATURE:
<223> OTHER INFORMATION: Chemically Synthesized
<220> FEATURE:
<223> OTHER INFORMATION: VII-49-B hexapeptide.
<220> FEATURE:
<221> NAME/KEY: MISC_FEATURE
<222> LOCATION: (2)..(3)
<223> OTHER INFORMATION: X is hPhe.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 40

Arg Xaa Xaa Arg Trp Arg
1               5

<210> SEQ ID NO 41
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: VII-67-A hexapeptide.
<220> FEATURE:
<221> NAME/KEY: MISC_FEATURE
<222> LOCATION: (1)..(1)
<223> OTHER INFORMATION: X is DAB.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 41

Xaa Tyr Tyr Arg Trp Arg
1               5

<210> SEQ ID NO 42
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: Base formula.

<400> SEQUENCE: 42

Arg Tyr Tyr Arg Trp Arg
1               5

<210> SEQ ID NO 43
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: Base sequence with terminal modifications.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
```

<222> LOCATION: (6)..(6)
<223> OTHER INFORMATION: C terminal modified to include NH2.

<400> SEQUENCE: 43

Arg Tyr Tyr Arg Trp Arg
1               5

<210> SEQ ID NO 44
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-12-B hexapeptide.
<220> FEATURE:
<221> NAME/KEY: MISC_FEATURE
<222> LOCATION: (2)..(2)
<223> OTHER INFORMATION: X is D-tyrosine.
<220> FEATURE:
<221> NAME/KEY: MISC_FEATURE
<222> LOCATION: (4)..(4)
<223> OTHER INFORMATION: X is D-arginine.
<220> FEATURE:
<221> NAME/KEY: MISC_FEATURE
<222> LOCATION: (1)..(1)
<223> OTHER INFORMATION: N terminal modified to include acetyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 44

Arg Xaa Tyr Xaa Trp Arg
1               5

<210> SEQ ID NO 45
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-15-A hexapeptide.
<220> FEATURE:
<221> NAME/KEY: MISC_FEATURE
<222> LOCATION: (1)..(1)
<223> OTHER INFORMATION: N terminal modified to include butryl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 45

Arg Tyr Tyr Arg Trp Arg
1               5

<210> SEQ ID NO 46
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-21-C hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

```
<400> SEQUENCE: 46

Ala Tyr Tyr Arg Trp Arg
1               5

<210> SEQ ID NO 47
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-23-B hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 47

Arg Ala Tyr Arg Trp Arg
1               5

<210> SEQ ID NO 48
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-25-B hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 48

Arg Tyr Ala Arg Trp Arg
1               5

<210> SEQ ID NO 49
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-27-B hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 49

Arg Tyr Tyr Ala Trp Arg
1               5

<210> SEQ ID NO 50
<211> LENGTH: 6
<212> TYPE: PRT
```

```
<213> ORGANISM: Artificial
<220> FEATURE:
<223> OTHER INFORMATION: Chemically Synthesized
<220> FEATURE:
<223> OTHER INFORMATION: IV-29-B hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 50

Arg Tyr Tyr Arg Ala Arg
1               5

<210> SEQ ID NO 51
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-31-B hexapeptide.
<220> FEATURE:
<221> NAME/KEY: MISC_FEATURE
<222> LOCATION: (1)..(1)
<223> OTHER INFORMATION: N terminal modified to include propionyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 51

Arg Tyr Tyr Arg Trp Ala
1               5

<210> SEQ ID NO 52
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-33-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 52

Ala Tyr Tyr Arg Trp Arg
1               5

<210> SEQ ID NO 53
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-35-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
```

```
<221> NAME/KEY: MISC_FEATURE
<222> LOCATION: (6)..(6)
<223> OTHER INFORMATION: C terminal modified to include NH2.

<400> SEQUENCE: 53

Arg Ala Tyr Arg Trp Arg
1               5

<210> SEQ ID NO 54
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-37-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 54

Arg Tyr Ala Arg Trp Arg
1               5

<210> SEQ ID NO 55
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-39-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 55

Arg Tyr Tyr Ala Trp Arg
1               5

<210> SEQ ID NO 56
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-41-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 56

Arg Tyr Tyr Arg Ala Arg
1               5
```

```
<210> SEQ ID NO 57
<211> LENGTH: 6
<212> TYPE: PRT
<213> ORGANISM: Artificial
<220> FEATURE:
<223> OTHER INFORMATION: Chemically Synthesized
<220> FEATURE:
<223> OTHER INFORMATION: IV-43-B hexapeptide.
<220> FEATURE:
<221> NAME/KEY: MISC_FEATURE
<222> LOCATION: (1)..(1)
<223> OTHER INFORMATION: N terminal modified to include hexanoyl.
<220> FEATURE:
<221> NAME/KEY: MISC_FEATURE
<222> LOCATION: (6)..(6)
<223> OTHER INFORMATION: C terminal modified to include NH2.

<400> SEQUENCE: 57

Arg Tyr Tyr Arg Trp Ala
1               5
```

NOCICEPTIN-BASED ANALGESICS

RELATED APPLICATIONS

This application is a continuation application of U.S. application Ser. No. 11/402,083 filed Apr. 11, 2006 by inventor Amrit K. Judd and entitled "Nociceptin-Based Analgesics." That application is a continuation application of U.S. application Ser. No. 10/268,020 filed Oct. 9, 2002 by inventor Amrit K. Judd and entitled "Nociceptin-Based Analgesics now U.S. Pat. No. 7,049,287." That application was related to and claimed the benefit of U.S. Provisional Patent Application Ser. No. 60/327,888, filed Oct. 9, 2001, of Amrit K. Judd entitled "Developments of Nociceptin-Based Analgesics." All three prior applications are incorporated herein by this reference.

BACKGROUND OF THE INVENTION

1. Field of the Invention

The present invention relates to analgesic compounds targeted to the ORL1 receptor. More specifically, the present invention relates to agonist and antagonist compounds targeted to the ORL1 receptor and methods for their use.

2. Description of Related Art

It has been estimated that as much as 30% of the population of the industrialized countries of the world suffers from some degree of chronic pain. Many individuals suffering from chronic pain are forced to incur significant direct medical and pharmaceutical expenses. Such individuals often also suffer losses in income and productivity. In the United States, it is estimated that the combined value of these losses and costs is in excess of $50 billion annually.

To address the pain experienced by these millions of individuals, a large industry has developed to provide medications for controlling pain. The market for these analgesic drugs, broadly classified as nonsteroidal anti-inflammatory drugs and opiates, has become the largest in the world, with sales revenues estimated to be as high as 4.4 billion in 1996.

The analgesics sold in this market are among the most widely used compounds in the history of medicine. These products come in many forms, and include natural compounds and synthetic compounds which work safely and with varying degrees of effectiveness to ease the impact of pain on an individual. Many of the compounds used for severe pain are opiates such as morphine and synthetic morphine analogs. These compounds have become widely used and understood.

Despite their effectiveness against severe pain, opiate compounds are administered with caution, and their use is often restricted to relatively short time periods as a result of the side-effects and limitations often connected with their use. Many patients experience gastrointestinal side-effects which limit their ability to tolerate the medication for long periods of time. Other patients develop tolerance to opiates over time, resulting in diminished relief when opiate use is prolonged. Additionally, opiates carry a high potential for addiction, thus further endangering a patient. Accordingly, a need exists for effective, nonaddicting analgesic compounds which cause few, if any, undesirable side effects.

Opiates include a large class of compounds that act on opiate receptors, thus modulating the pain response in an individual. Three main subclasses of opiate receptors have been identified through binding studies, in vitro and in vivo pharmacology, autoradiography, and receptor cloning. Evans et al., Science, 258:1952-1955 (1992); Kieffer et al., Proc. Natl. Acad. Sci. USA, 89:12048-12052 (1992); Chen et al., Mol. Pharmacol., 44:8-12 (1993); Wang et al., Proc. Natl. Acad. Sci. USA, 90:10230-10234 (1993); and Yasuda et al., Proc. Natl. Acad. Sci. USA, 90:16736-16740 (1993). The $\mu$, $\delta$, and $\kappa$ receptors are the apparent receptors acted upon by common opiate drugs.

During research aimed at characterizing opioid receptors, a closely-related orphan receptor eventually designated opioid receptor like 1 ("ORL1") was identified. Mollereau et al., FEBS Lett., 341:33-38 (1994); Wang et al., FEBS Lett., 348:75-79 (1994); Bunzow et al., FEBS Lett., 347:284-288 (1994). Despite levels of homology with the $\mu$, $\delta$, and $\kappa$ receptors similar to their own homology to each other, the ORL1 receptor failed to bind opiate compounds with high affinity. Although etorphine and some dynorphin gene products do produce a 1000-fold higher-than-expected response when exposed to ORL1, ORL1's failure to bind with other opiates demonstrates that though ORL1 is in the opiate receptor family, it is not a true opiate receptor. Zhang and Yu, J. Biol. Chem., 270:22772-22776 (1995).

In 1995, an endogenous ligand for ORL1 was sequenced. Meunier et al., Nature, 377:532-555 (1995). The peptide ligand, called nociceptin, is a 17-amino-acid peptide with a sequence resembling that of some opioid peptides, including dynorphin. Nociceptin was shown to inhibit cAMP accumulation in CHO cells transfected with ORL1, while causing no change in non-transfected parent cells.

In other studies, nociceptin showed low affinity for the $\mu$, $\delta$, and $\kappa$ opioid receptors. Gintzler et al., Eur. J. Pharmacol., 325:29-34 (1997). Nociceptin also stimulates [$^{35}$S] GTP$\gamma$S binding in transfected cells and inhibits electrically-induced contractions in mouse vas deferens (MVD); and, to a lesser extent, in guinea pig ileum (GPI). Berzetei-Gurske et al., Eur. J. Pharmacol., 302:R1-R2 (1996). Further studies showed that intracerebroventricular injections of nociceptin decreases hot plate escape jumping latency and a decrease in tail flick latency in mice. Meunier et al., Nature, 377:532-555 (1995); and Reinscheid et al., Science, 270:792-794 (1995).

Intrathecal administration of nociceptin also shows promising use. When administered to the spinal cord in the presence of morphine, the action of morphine is inhibited, and further, nociceptin has analgesic action in tail flick testing in mice and also increases morphine analgesia. Tian et al., Br. J. Pharmacol., 120:676-680 (1997). Nociceptin has also been shown to be involved in peripheral analgesia, inhibiting formalin pain when administered intrathecally. Yamamoto et al., Neurosci., 81:249-254 (1997). It similarly acts analgesically when administered to rats in a hot plate test of rats with a chronic constriction injury, a model of neuropathic pain. Yamamoto et al., Neurosci. Lett., 224:107-110 (1997). Similar function was observed in models of chronic pain, and in diabetic mice. Kamei et al., Eur. J. Pharmacol., 370:109-116 (1999).

The results of these and other tests suggest that agonists of the nociceptin receptor may prove useful as non-opioid analgesics, potentially useful with neuropathic pain. Additionally, the results suggest that antagonists of the nociceptin receptor may likely exhibit anti-anxiety properties. Unfortunately, however, nociceptin, the natural ligand for ORL1, is difficult to administer to a patient, and once administered, nociceptin is very susceptible to the action of proteases. Accordingly, a need exists for compounds which act as agonists and antagonists of the ORL1 receptor that are more easily administered to a patient, and that are resistant to protease activity.

In more recent years, the pain medication market has expanded very rapidly with the entry of COX-II inhibitors for use with arthritic pain. The novel NSAID medications Vioxx® made by Merck Inc., and Celebrex® made by Pfizer/Pharmacia have garnered huge popularity and widespread use in combating pain. The sales of Celebrex® in 2001 alone were 3.1 billion dollars. These drugs have been shown to avoid some of the gastrointestinal problems of traditional NSAIDS while providing good relief to patients. Some researchers remain concerned about the prospective cardiovascular side-effects of these drugs, however. Additionally, as with opioid medications, these NSAIDS are generally ineffective against neuropathic pain. Neuropathic pain is a condition often thought to stem from damage to nerves, and is often found in diabetic patients. As diabetes levels continue to swell in the United States, it becomes obvious that a need exists for novel compounds which are effective against neuropathic pain which are not found in the current analgesic market.

Most known analgesic compounds are agonists of at least one of a group of opioid receptors. These compounds bind to the receptor, stimulating pain relief. Other known compounds share a similar structure, but merely compete for binding with agonist compounds. These competitive compounds are referred to as antagonists. Antagonist compounds often exhibit anxiety-relieving, or "anxiolytic" properties when administered to a patient. The high incidence of anxiety disorders suggests that it would be a benefit to characterize novel anxiolytic compounds.

Finally, recent research has shown that some compounds currently used for their analgesic properties also exhibit anti-cancer activity. Despite recent advances in medical technology and breakthroughs in molecular medicine, cancer remains a difficult disease to treat. As a result, any novel compound with anti-cancer properties is a welcomed improvement in the art.

Thus, it would be an improvement in the art to provide compounds including agonists and antagonists of the ORL1 receptor. Further, it would be a benefit to provide novel compounds for use as analgesics. Similarly, it would be an improvement in the art to provide novel compounds for use as anxiolytic agents. It would also be an improvement to provide novel compounds with anti-cancer properties.

Such compounds and methods of their use are disclosed herein.

SUMMARY OF THE INVENTION

The present invention has been developed in response to the present state of the art, and in particular, in response to the problems and needs in the art that have not yet been fully solved by currently available analgesic compounds. Thus, the present invention provides compounds such as nociceptin agonists and antagonists for use as analgesic agents.

The invention includes a family of hexapeptide nociceptin analogs including compounds exhibiting full agonist activity and full antagonist activity. The antagonist peptide has been shown to potentiate morphine analgesia and possess some analgesic activity when used alone.

The invention includes compounds sharing the general formula:

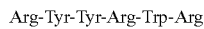

Arg-Tyr-Tyr-Arg-Trp-Arg (SEQ ID NO: 42) The compounds of the invention include compounds having substitutions to any one or two positions of the above formula. Specifically, the compounds of the invention include compounds having non-conservative substitutions and conservative substitutions, where conservative substitutions involve the replacement of an amino acid by one with similar characteristics such that the substitution is unlikely to substantially change the shape or properties of the peptide. One example of conservative substitution is the substitution of one hydrophobic amino acid for another. Other substitutions are non-conservative in nature. Still other substituted hexapeptides according to the invention have non-natural, or modified amino acids substituted into the place of a natural or substituted amino acid. Finally, the compounds of the invention include hexapeptides with modifications to the amino-terminus and/or carboxy-terminus of the hexapeptide.

One set of compounds of the invention includes compounds having the formula: Arg-Xaa-Tyr-Arg-Trp-Arg (SEQ ID NO: 17). In these compounds, "Xaa" is used to denote an amino acid substitution. Suitable substitutions include other natural amino acids, modified amino acids, and amino acid analogs. In one family of embodiments, the hexapeptides include a modified Phe amino acid molecule in the Xaa position. In some specific embodiments of the hexapeptide, Xaa is an amino acid selected from the group consisting of Phe (4-Me) SEQ ID NO: 1, Phe (4-COOH) SEQ ID NO: 2, Phe (4-NO$_2$) SEQ ID NO: 3, Phe (4-F) SEQ ID NO: 4, Phe (4-CN) SEQ ID NO: 6.

In another family of hexapeptides according to the invention, Xaa is a modified Tyr amino acid molecule. In specific embodiments, "Xaa" may be an amino acid molecule selected from the group consisting of Tyr (4-Me) SEQ ID NO: 5, Tyr (3-Cl) SEQ ID NO: 7, and Tyr (BN, 3-Cl) SEQ ID NO: 23.

Another set of compounds of the invention includes compounds having the formula: Arg-Tyr-Xaa-Arg-Trp-Arg (SEQ ID NO: 18). As above, "Xaa" denotes an amino acid substitution. Suitable substitutions include other natural amino acids, modified amino acids, and amino acid analogs. In one family of embodiments, the hexapeptides include modified Phe amino acid molecules in the Xaa position. In some specific embodiments of the hexapeptide, Xaa is an amino acid selected from the group consisting of Phe (4-F) SEQ ID NO: 12, Phe (NO$_2$) SEQ ID NO: 13, hPhe (2, 4 di-NO$_2$) SEQ ID NO: 20, Phe (4-CH$_2$SO$_3$H) SEQ ID NO: 21, Phe (4—NHAc) SEQ ID NO: 16, and Phe (4-CH$_2$NH$_2$) SEQ ID NO: 22.

In another family of hexapeptides according to the invention, Xaa is a modified Tyr amino acid molecule. In specific embodiments, Xaa may be an amino acid molecule selected from the group consisting of Tyr (2, 6 di-Me) (SEQ ID NO: 15).

The invention further includes yet another set of hexapeptides, these being according to the formula: Xaa$_1$-Tyr-Tyr-Xaa$_2$-Trp-Xaa$_3$ (SEQ ID NO: 19). In this family of hexapeptides, "Xaa$_1$", "Xaa$_2$", and "Xaa$_3$" are used to denote either the placement of Arg, or of an amino acid substitution. Hexapeptides within this group may have Arg at two of the three positions and a substitution at the third. Alternatively, hexapeptides may have substitutions at two of the three positions and Arg only at the remaining position. Finally, the hexapeptide may have substitutions at all three positions. As above, suitable substitutions include other natural amino acids, modified amino acids, and amino acid analogs. In some specific embodiments of the hexapeptide, Xaa$_1$, Xaa$_2$, and Xaa$_3$ are selected from the group consisting of Arg, ε-aminocaproyl, DAP, and DAB. In one such hexapeptide, Xaa$_1$ is ε-aminocaproyl, Xaa$_2$ is Arg, and Xaa$_3$ is Arg (SEQ ID NO: 9). In another, Xaa$_1$ is Arg, Xaa$_2$ is ε-aminocaproyl, and Xaa$_3$ is Arg (SEQ ID NO: 10). In still another, Xaa$_1$ is Arg, Xaa$_2$ is Arg, and Xaa$_3$ is ε-aminocaproyl (SEQ ID NO: 11). In another, Xaa$_1$ is DAP, Xaa$_2$ is Arg, and Xaa$_3$ is Arg (SEQ ID NO: 14). In yet another, Xaa$_1$ is DAB, Xaa$_2$ is Arg, and Xaa$_3$ is Arg (SEQ ID NO: 24).

Still another set of hexapeptide compounds according to the invention include compounds having the formula: Arg-Tyr-Tyr-Arg-Xaa-Arg (SEQ ID NO: 27). In these compounds, "Xaa" is used to denote an amino acid substitution. Suitable substitutions include other natural amino acids, modified amino acids, and amino acid analogs. In one family of hexapeptides of the invention, the Xaa is a modified Trp amino acid molecule. In a specific embodiment of the invention, Xaa is Trp (5-CN) (SEQ ID NO: 8).

In addition to the amino acid substitutions outlined above, the hexapeptides of the invention may include amino-terminal and/or carboxy-terminal modifications. Hexapeptides according to the invention may include modifications to both the amino and carboxy-termini, or alternatively may be made to only one terminus. In some embodiments, the amino terminus is modified to include a moiety selected from the group consisting of optionally substituted straight-chain alkyls, optionally substituted branched chain alkyls, aralalkyls, cycloalkyls, or alkylcycloalkyls containing from about 1 to about 12 carbon atoms. In some preferred embodiments, the amino terminus of the peptide is acetylated.

The hexapeptides of the invention may additionally, or alternatively, be modified at the carboxy terminus. The carboxy-terminal modifications may include an amine group, a carboxy group, a hydroxy group, and aldehydes. Alternatively, the carboxy terminus of the hexapeptides may be modified to include substituted or non-substituted straight-chain alkyls, branched chain alkyls, aralalkyls, cycloalkyls, or alkylcycloalkyls containing from about 1 to about 12 carbon atoms.

The invention further includes pharmaceutical compositions comprising one or more of the hexapeptides of the invention. Such pharmaceutical compositions may additionally include a pharmaceutically acceptable diluent or excipient. Such a diluent or excipient may ease delivery and/or protect the hexapeptides from degradation during storage or administration.

The invention additionally includes methods of treating pain, including neuropathic pain. These methods comprise administering a compound comprising the hexapeptides of the invention to a patient in need of analgesia.

These and other features and advantages of the present invention will become more fully apparent from the following description and appended claims, or may be learned by the practice of the invention as set forth hereinafter.

BRIEF DESCRIPTION OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
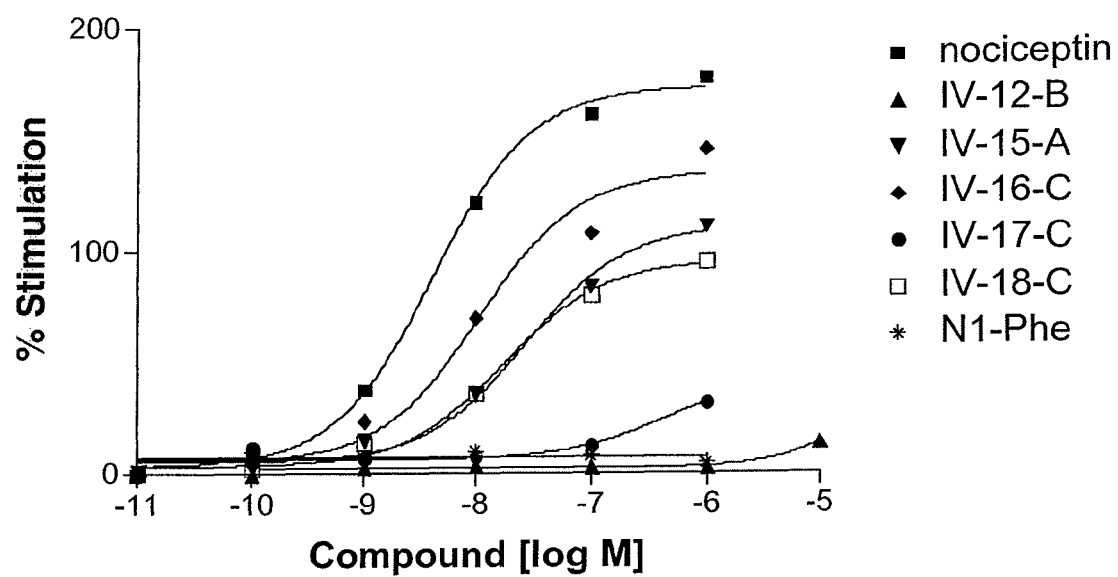
FIG. 1 is a chart showing the binding affinity of [$^{35}$S] GTPγS induced by nociceptin, modified hexapeptides of the invention, and $N^1$-Phe-nociceptin (1-13)NH$_2$.

The following detailed description of the embodiments of the hexapeptides of the present invention, as represented in FIGS. 1 through 18, is not intended to limit the scope of the invention, as claimed, but is merely representative of presently preferred embodiments of the invention.

The ORL-1 receptor and its natural ligand, nociceptin, provide a novel target for analgesic compounds. Animal studies have been conducted to confirm the usefulness of nociceptin agonists or antagonists with this target in analgesic applications. These tests showed that agonists or antagonists do exhibit analgesic properties. Specific testing showed effectiveness of such compounds as an analgesic in models of neuropathic pain. Yamamoto et al., *Neurosci. Lett.*, 224: 107-110 (1997).

Novel agonists and antagonists have been developed and are disclosed herein. These compounds have been tested to more clearly characterize the effect of ORL1 activation and inhibition on analgesic and other opioid systems. These newly discovered antagonists may later be used to determine whether nociceptin has constitutive activity in mammalian brain, as well as whether an ORL1 receptor antagonist will act as a non-addicting analgesic. Further, the compounds of the invention may exhibit diuretic properties, as well as cancer-fighting ability.

As noted above, the identification and characterization of high-affinity compounds furthers the development of a better understanding of the actions of nociceptin and its receptor ORL1. The physiological actions of nociceptin are poorly understood in part because of the absence of low molecular weight, stable agonists and high-affinity antagonists. Although initial testing showed that nociceptin decreased tail flick latencies in rats, and further that it inhibited opiate analgesia, further testing has begun to show that the physiological actions of nociceptin may be very complicated. Some studies showed the anti-opiate activity of nociceptin to potentially be region- and assay-specific. In one study, nociceptin was found to be analgesic in the spinal cord. Tian et al., *Br. J. Pharmacol.*, 120:676-680 (1997); Xu et al, *Neuroreport*, 7:2092-2094 (1996). Additionally, as noted above, it has also been reported to be an effective analgesic in a model of chronic pain. Yamamoto et al., *Neurosci. Lett.*, 224: 107-110 (1997). In addition, nociceptin exhibits significantly greater potency as an analgesic when used in diabetic mice than when used in non-diabetic mice. Kamei, et al., *Eur. J. Pharmacol.*, 370:109-116 (1999). In contrast, it has also been shown to induce allodynia, a condition in which normal non-painful stimuli cause pain, when injected into the spinal cord. Hara et al., *Br. J. Pharmacol.*, 121:401-408 (1997).

For research purposes, the development of antagonists will be even more valuable. As with opiate receptors, and now with tetrahydrocannabinol (THC) receptors, the availability of an antagonist allows for a better understanding of the specific actions of a compound. Opiate actions are currently defined by their ability to be antagonized by naloxone. It is anticipated that the same criteria apply for ORL1. The availability of an antagonist also aids in the identification of any constitutive actions of nociceptin-ORL1, or in vivo actions brought on by altered physiologic states. For instance, naloxone has no effects on analgesia in naive animals, but it does have important effects with respect to cerebral glucose utilization in specific brain regions. Kraus et al., *Brain Res.*, 724:33-40 (1996). These experiments demonstrate regions of endogenous opiate activity in untreated animals. Of course, naloxone has significant and well known effects in animals with altered physiologic states, including the precipitation of withdrawal and the inhibition of stress-induced analgesia. Antagonists to ORL1 will undoubtedly uncover many actions of nociceptin in normal and altered states.

The invention thus provides hexapeptide compounds which interact with the ORL-1 receptor (hereinafter, the "nociceptin receptor"), including compounds exhibiting agonist and antagonist properties. The hexapeptides of the invention may be constructed solely of natural amino acids. Alternatively, the hexapeptides may include non-natural amino acids including, but not limited to, modified amino acids. Modified amino acids include natural amino acids which have been chemically modified to include a group or groups not naturally present on the amino acid. The hexapeptides of the invention may additionally include D-amino acids. Still further, the hexapeptides of the invention may include amino acid analogs.

A first group of these compounds were constructed having the general formula:

Arg-Tyr-Tyr-Arg-Trp-Arg

These compounds contained various amino- and carboxy-terminal modifications and an amino acid substitution, as shown in Table 1.

TABLE 1

Binding Affinity and Functional Activity of Compounds at ORL1.

| Compound | SEQ ID NO: | [³H]nociceptin Binding IC$_{50}$ (nM) | [³⁵S]GTPγS Binding EC$_{50}$ (nM) | Percent Stimulation |
|---|---|---|---|---|
| Nociceptin | | 1.0 | 4.2 | 100 |
| Ac-RYYRWR-NH$_2$ | 43 | 0.72 | 1.2 | 100 |
| IV-12-B Ac-RY(D)YR(D)WRNH$_2$ | 44 | 1145 | >10,000 | <10 |
| IV-15-A Butyl-RYYRWR-NH$_2$ | 45 | 4.3 | 35.3 | 63 |
| IV-16-C Propionyl-RYYRWR-NH$_2$ | 24 | 1.2 | 22.3 | 82 |
| IV-17-C Hexanoyl-RYYRWR-NH$_2$ | 25 | 2.6 | * | 18 |
| IV-18-C Heptanoyl-RYYRWR-NH$_2$ | 26 | 2.6 | 16.9 | 54 |

* Difficult to determine due to low efficacy.

The compounds of Table 1 were tested for [³⁵S]GTPγS stimulation similar to that induced by nociceptin. The results of this testing are shown in the chart in FIG. 1. Nociceptin stimulates [³⁵S]GTPγS to bind to membranes derived from CHO cells transfected with human ORL-1. The compounds of Table 1 were tested in a [³⁵S]GTPγS binding assay to determine their ability to stimulate [³⁵S]GTPγS binding in comparison to nociceptin.

The [35S]GTPγS binding assays were conducted generally as described by Traynor and Nahorski (1995). First, CHO cells transfected with human ORL-1 are scraped from tissue culture dishes into 20 mM HEPES, 1 mM EDTA, and then centrifuged at 500×g for 10 minutes. The cells are then re-suspended in this buffer and homogenized using a Polytron Homogenizer.

The cellular homogenate is next centrifuged at 20,000×g for 20 minutes. Following this, the resulting pellet is re-suspended in a buffer containing 20 mM HEPES, 10 mM MgCl$_2$, and 100 mM NaCl, having a resulting pH of 7.4. The suspension is then re-centrifuged at 20,000×g and suspended once more in the above-listed buffer. The pellet may be frozen at −70° C. prior to the final centrifugation. For the binding assay, membranes (10-20 μg protein) are incubated with [³⁵S] GTPγγS (50 pM), GDP (usually 10 μM), and the desired compound. The total volume of the mixture is 1 ml, which is incubated for 60 min at 25° C.

Following incubation, samples are filtered over glass fiber filters and counted. A dose response with the full agonist nociceptin may then be conducted in each experiment to identify full and partial agonist compounds.

As seen in FIG. 1 and Table 1, IV-16-C (SEQ ID NO: 24), having the structure Propionyl-RYYRWR-NH$_2$ exhibited high affinity and appeared to be a potent, nearly full agonist of ORL-1. In contrast, compound IV-17-C (SEQ ID NO: 25), having the structure Hexanoyl-RYYRWR-NH$_2$ maintains high affinity but is a very low efficacy compound.

As seen in FIG. 1, the antagonist properties of IV-17-C (SEQ ID NO: 25) can readily be observed in its ability to inhibit the stimulation of [$^{35}$S]GTPγS binding induced by 10 nM nociceptin. The 20% stimulation found at 1 and 10 μM of [$^{35}$S]GTPγS confirms the partial agonist activity of this compound, as also seen in FIG. 1 and shown in Table 1.

Figure 2:
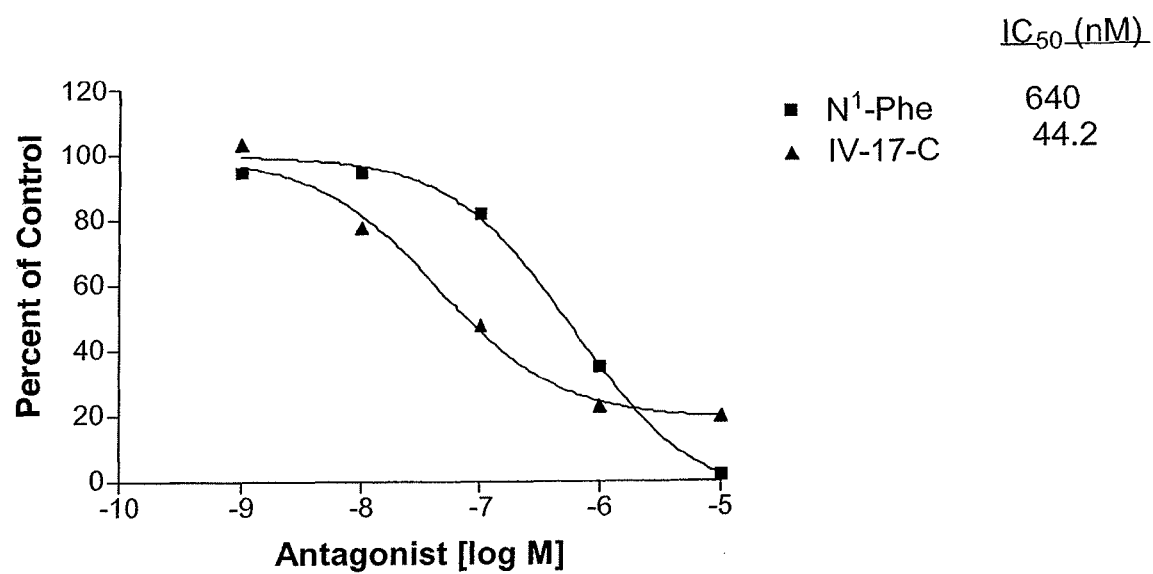
FIG. 2 is a chart showing the antagonist properties of IV-17-C (SEQ ID NO: 25), as shown by its ability to inhibit the stimulation of [$^{35}$S]GTPγS binding by nociceptin.

In addition, as seen in FIG. 2, IV-17-C (SEQ ID NO: 25) is at least 10 times more potent as an antagonist than the complete antagonist N$^1$-Phe-nociceptin (1-13)NH$_2$ reported in Calo et al., 2000. N$^1$-Phe-nociceptin (1-13)NH$_2$ is a recently-developed peptide antagonist that has been shown to potentiate morphine analgesia and to possess some analgesic activity on its own. IV-17-C (SEQ ID NO: 25) was tested in vivo for analgesic activity and for potentiation of morphine analgesia. This testing showed no measurable in vivo activity. Without being limited to any one theory, it was concluded that the apparent in vivo inactivity of the molecule is likely attributable to its rapid in vivo degradation. These studies suggest that IV-17-C (SEQ ID NO: 25) is a very promising lead, for which more stable analogs have potential as analgesic compounds.

Based upon the activity of the compounds discussed above, additional compounds were synthesized. These compounds were varied in order to identify residues which must be conserved in order to retain binding affinity and functional activity. Thus, the group consisted of molecules resulting from "alanine scans" of the high affinity agonist IV-16-C (SEQ ID NO: 24) and the antagonist IV-17-C (SEQ ID NO: 25). In these alanine scans, the original sequences, Propionyl-RYYRWR-NH$_2$ (SEQ ID NO: 24) and Hexanoyl-RYYRWR-NH$_2$ (SEQ ID NO: 25) were systematically modified by substituting an alanine amino acid into every position of the hexapeptide, one amino acid at a time. The binding affinities of these alanine scan molecules are shown in Table 2.

TABLE 2

Binding Affinities of Alanine Scan of IV-16-C and IV-17-C.

| Compound | SEQ ID NO: | IC$_{50}$ (nM) |
|---|---|---|
| IV-21-C Propionyl-AYYRWR-NH$_2$ | 46 | 1780 |
| IV-23-B Propionyl-RAYRWR-NH$_2$ | 47 | 182 |
| IV-25-B Propionyl-RYARWR-NH$_2$ | 48 | 495 |
| IV-27-B Propionyl-RYYAWR-NH$_2$ | 49 | 400 |
| IV-29-B Propionyl-RYYRAR-NH$_2$ | 50 | 1890 |
| IV-31-B Propionyl-RYYRWA-NH$_2$ | 51 | 76 |
| IV-33-B Hexanoyl-AYYRWR-NH$_2$ | 52 | 1015 |
| IV-35-B Hexanoyl-RAYRWR-NH$_2$ | 53 | 113 |
| IV-37-B Hexanoyl-RYARWR-NH$_2$ | 54 | 79 |
| IV-39-B Hexanoyl-RYYAWR-NH$_2$ | 55 | 1000 |
| IV-41-B Hexanoyl-RYYRAR-NH$_2$ | 56 | 710 |
| IV-43-B Hexanoyl-RYYRWA-NH$_2$ | 57 | 311 |
| Nociceptin | | 1.3 |

The data in Table 2 indicate the importance of each residue in the parent peptide, Ac-RYYRWR-NH$_2$, even with the lipophilic addition to the amino terminals. Even in the best cases, binding affinities dropped by a factor of at least 30.

Figure 3:
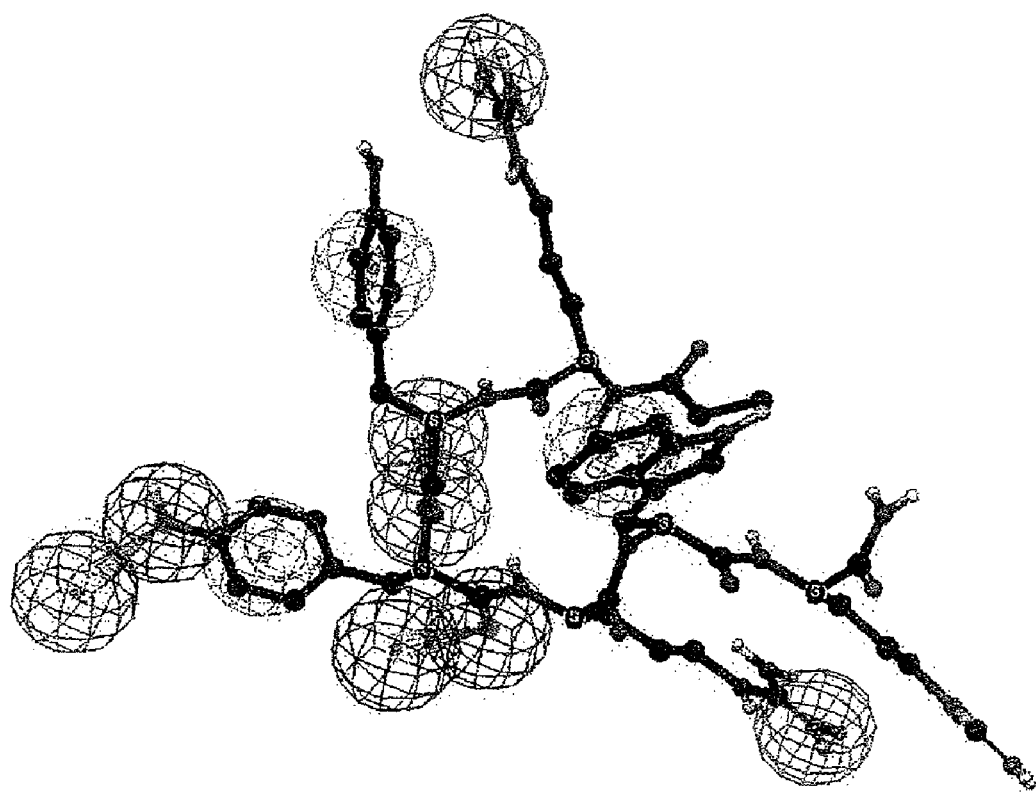
FIG. 3 shows the conformation of the agonist IV-16-C (SEQ ID NO: 24) of the invention in comparison with a hypothesized nociceptin pharmacophore structure.
Figures 4A, 4B:
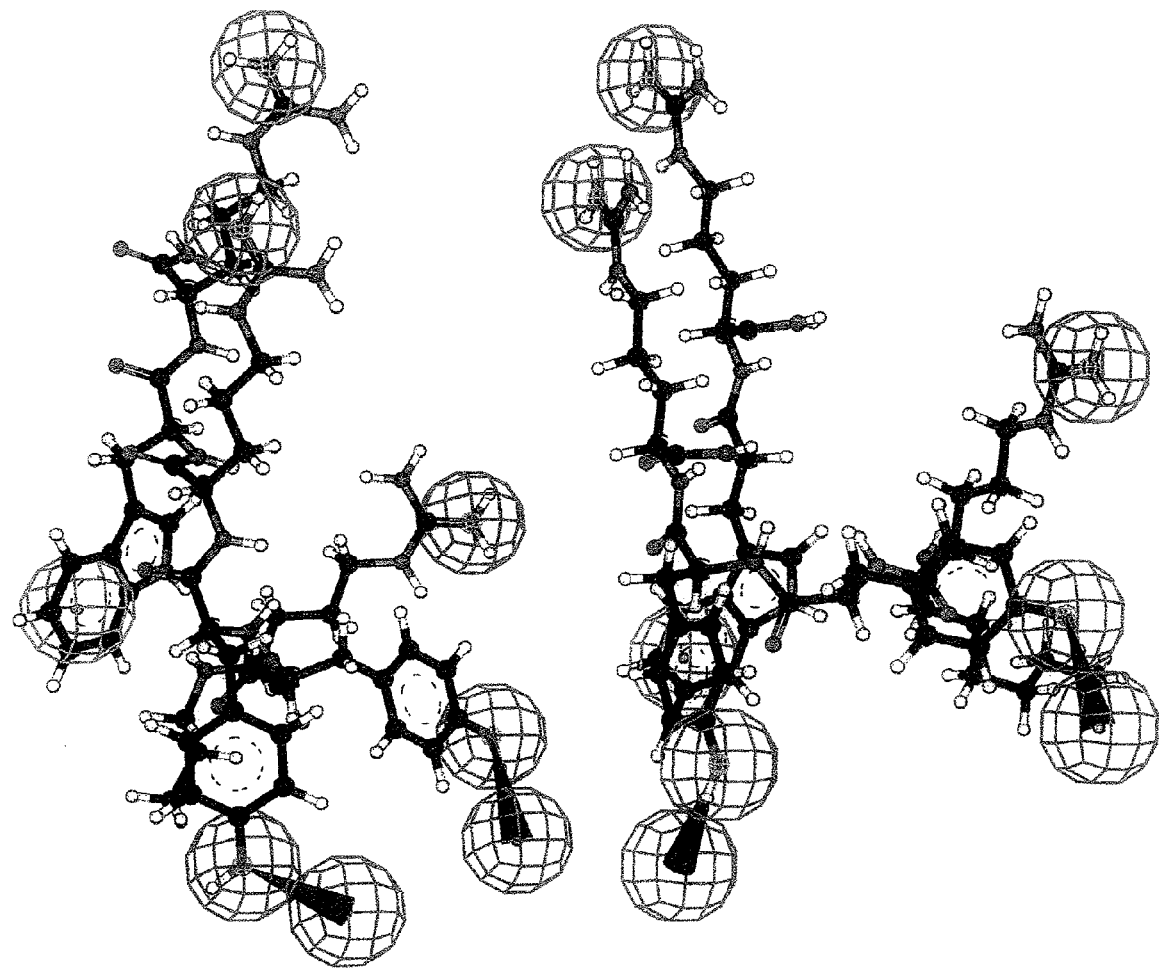
FIG. 4A shows the 3-dimensional hypothetical pharmacophore derived from IV-16-C (SEQ ID NO: 24)
FIG. 4B shows the 3-dimensional hypothetical pharmacophore derived from IV-17-C (SEQ ID NO: 25)

The IV-16-C (SEQ ID NO: 24) agonist was then subjected to computational studies. First the hexapeptide molecule was modeled in a random conformation using software model building and energy refinement tools. The software utilized was CATALYST, from Molecular Simulations, Inc. These structural models were used to create an arbitrary 3-dimensional pharmacophore model. This was done using the functional mapping capability of the molecular modeling program used in the "view hypothesis workbench" mode of CATALYST. FIG. 3 shows the 3-dimensional conformation of the IV-16-C peptide overlapped with the 3-dimensional structure of the hypothetical agonist pharmacophore.

These preliminary computational studies were conducted with no data available about the structure of the peptide that had been deduced from experimental sources (NMR, X-ray). As a result, a completely random conformation was chosen for the purpose of illustration in FIG. 3.

The IV-16-C (SEQ ID NO: 24) peptide studied above is a very flexible molecule and in principle may likely adopt many low energy conformations, due to the fact that it is endowed with at least 15 rotatable bonds. Pharmacophore generation methods in CATALYST are sensitive to the conformational models employed. Hence, the choice of the pharmacophore for the purpose of illustrations of database search methods is purely random. The actual pharmacophore structure may be derived based on an experimental structure for such flexible molecules.

The pharmacophore may be deduced by conducting a conformational search to find molecules similar to leading compounds such as IV-16-C (SEQ ID NO: 24) and creating a multi-conformation 3-dimensional database of the molecules. The compound may then be subjected to an alignment to fit, and the quality of the molecules categorized be assessed with respect to the lead compounds. These data help to generate a pharmacophore model, which may then be studied using databases such as the Available Chemical Directory (ACD), BioByte Master File, National Cancer Institute Database (NCI), The Derwent World Drug Index, and the Maybridge catalog. Accuracy may then be assessed by producing or locating molecules conforming to the pharmacophore model, mapping between the pharmacophore model and the new molecules, predicting the activity of the new molecules based on the pharmacophore, and synthesizing and assaying the more promising drug candidates.

Following the above plan, a series of peptide analogs was generated for testing. These analogs incorporated amino acid replacements using commercially-available non-natural amino acids. The sequences of these analogs are listed in Table 3.

TABLE 3

Sequences of the Peptides Synthesized in Year 02

| Peptide No. | SEQ ID NO: | Sequence |
|---|---|---|
| VII-1-A | 28 | Nipacotyl-Arg-Tyr-Tyr-Arg-Trp-Arg-NH$_2$ |
| VII-2-A | 29 | β-Nva-Arg-Tyr-Tyr-Arg-Trp-Arg-NH$_2$ |
| VII-3-A | 30 | β-aminoisobutryl-Arg-Tyr-Tyr-Arg-Trp-Arg-NH$_2$ |
| VII-4-B | 31 | 1-aminocyclohexanoyl-Arg-Tyr-Tyr-Arg-Trp-Arg-NH$_2$ |
| VII-7-B | 26 | Pentanoyl-Arg-Tyr-Tyr-Arg-Trp-Arg-NH$_2$ |
| VII-11-B | 32 | Ac-Arg-Phg-Phg-Arg-Trp-Arg-NH$_2$ |
| VII-13-B | 33 | Ac-Arg-Tyr-Phg-Arg-Trp-Arg-NH$_2$ |
| VII-15-B | 1 | Ac-Arg-Phe(4-Me)-Tyr-Arg-Trp-Arg-NH$_2$ |
| VII-17-B | 34 | Ac-Arg-Phe(4-Me)-Phe(4-Me)-Arg-Trp-Arg-NH$_2$ |
| VII-19-B | 2 | Ac-Arg-Phe(4-COOH)-Tyr-Arg-Trp-Arg-NH$_2$ |
| VII-21-C | 35 | Ac-Arg-Phe(4-COOH)-Phe(COOH)-Arg-Trp- |

TABLE 3-continued

Sequences of the Peptides Synthesized in Year 02

| Peptide No. | SEQ ID NO: | Sequence |
|---|---|---|
| | | Arg-NH$_2$ |
| VII-23-B | 3 | Ac-Arg-Phe(NO$_2$)-Tyr-Arg-Trp-Arg-NH$_2$ |
| VII-27-B | 36 | Ac-Arg-Phe(SO$_3$H)-Tyr-Arg-Trp-Arg-NH$_2$ |
| VII-29-B | 37 | Ac-Arg-Phe(4-SO$_3$H)-Tyr-Arg-Trp-Arg-NH$_2$ |
| VII-31-B | 4 | Ac-Arg-Phe(4-F)-Tyr-Arg-Trp-Arg-NH$_2$ |
| VII-33-B | 38 | Ac-Arg-Phe(4-F)-Phe(4-F)-Arg-Trp-Arg-NH$_2$ |
| VII-35-C | 5 | Ac-Arg-Tyr(4-Me)-Tyr-Arg-Trp-Arg-NH$_2$ |
| VII-37-B | 39 | Ac-Arg-Tyr(4-Me)-Tyr(4-Me)-Arg-Trp-Arg-NH$_2$ |
| VII-39-D | 7 | Ac-Arg-Tyr(BN*, 3-Cl)-Tyr-Arg-Trp-Arg-NH$_2$ |
| VII-43-C | 6 | Ac-Arg-Phe(4-CN)-Tyr-Arg-Trp-Arg-NH$_2$ |
| VII-49-B | 40 | Ac-Arg-hPhe-hPhe-Arg-Trp-Arg-NH$_2$ |
| VII-51-A | 8 | Ac-Arg-Tyr-Tyr-Arg-Trp(5-CN)-Arg-NH$_2$ |
| VII-53-B | 9 | Ac-ε-aminocaproyl-Tyr-Tyr-Arg-Trp-Arg-NH$_2$ |
| VII-55-A | 10 | Ac-Arg-Tyr-Tyr-ε-aminocaproyl-Trp-Arg-NH$_2$ |
| VII-57-C | 11 | Ac-Arg-Tyr-Tyr-Arg-Trp-ε-aminocaproyl-NH$_2$ |
| VII-61-B | 12 | Ac-Arg-Tyr-Phe(4-F)-Arg-Trp-Arg-NH$_2$ |
| VII-63-B | 13 | Ac-Arg-Tyr-Phe(4-NO$_2$)-Arg-Trp-Arg-NH$_2$ |
| VII-65-F | 14 | Ac-Dap-Tyr-Tyr-Arg-Trp-Arg-NH$_2$ |
| VII-67-A | 41 | Ac-Dab-Tyr-Tyr-Arg-Trp-Arg-NH$_2$ |
| VII-71-B | 20 | Ac-Arg-Tyr-hPhe(2,4-di-NO$_2$)-Arg-Trp-Arg-NH$_2$ |
| VII-73-A | 15 | Ac-Arg-Tyr-Tyr(2,6-di-Me)-Arg-Trp-Arg-NH$_2$ |
| VII-75-B | 21 | Ac-Arg-Tyr-Phe(4-CH$_2$SO$_3$H)-Arg-Trp-Arg-NH$_2$ |
| VII-77-A | 16 | Ac-Arg-Tyr-Phe(4-NHAc)-Arg-Trp-Arg-NH$_2$ |
| VII-79-A | 22 | Ac-Arg-Tyr-Phe(4-CH$_2$NH$_2$)-Arg-Trp-Arg-NH$_2$ |
| VII-87-B | 23 | Ac-Arg-Tyr(3-Cl)-Tyr-Arg-Trp-Arg-NH$_2$ |

BN = Benzyl

All of the peptides listed above in Table 3 were next synthesized using Merrifield's Solid Phase technique on a CS Bio 136 Peptide Synthesizer. Fmoc-Rink-Amide resin was purchased from AnaSpec (San Jose, Calif.). Fmoc amino acids were purchased from AnaSpec or PerSeptive Biosystems (Foster City, Calif.). The non-natural or unusual amino acids needed were purchased from RSP Amino Acids Analogues Inc. The purity of peptides was checked by analytical high pressure liquid chromatography (HPLC) and Mass Spectroscopy and they were greater than 95% pure.

Figure 5A:
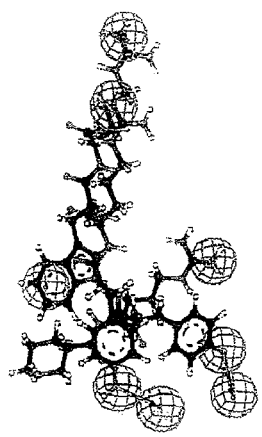
FIGS. 5A-5W compare the predicted structure of a group of peptide analogs of the invention in comparison with the pharmacophore hypothesis for IV-16-C (SEQ ID NO: 24)
Figure 5B:
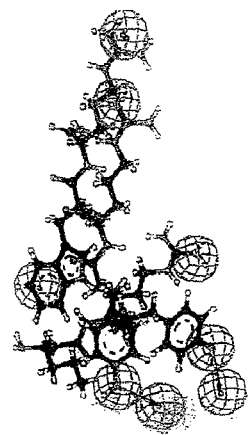
Figure 5C:
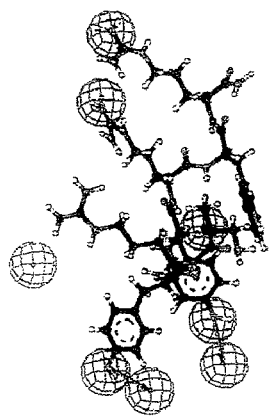
Figure 5D:
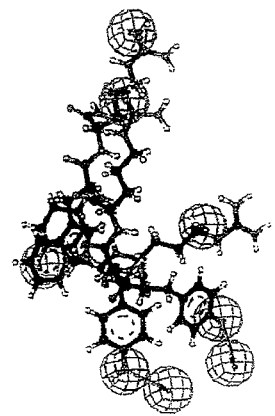
Figure 5E:
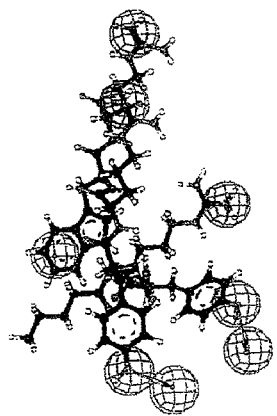
Figure 5F:
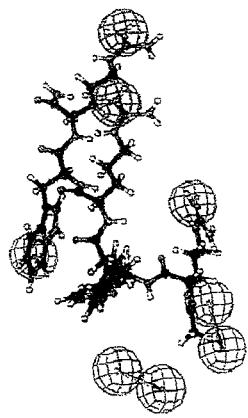
Figure 5G:
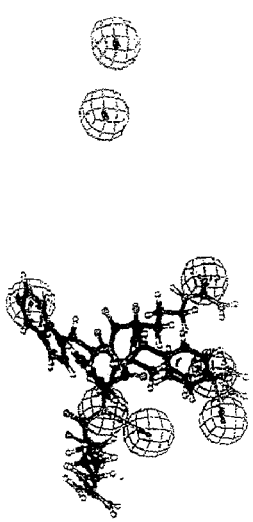
Figure 5H:
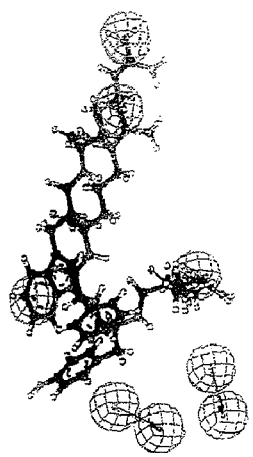
Figure 5I:
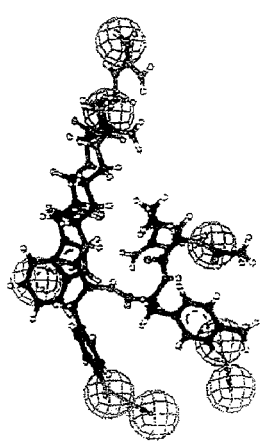
Figure 5J:
Figure 5K:
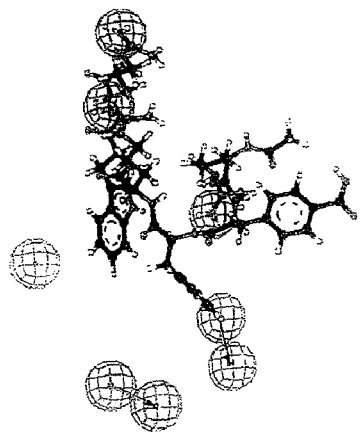
Figure 5L:
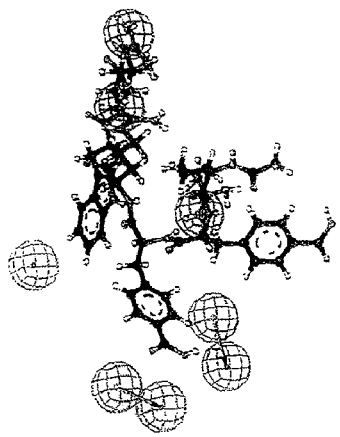
Figure 5M:
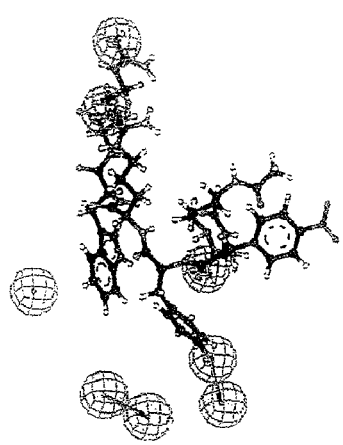
Figure 5N:
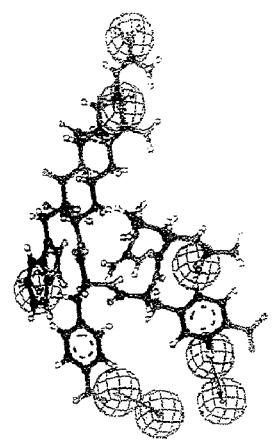
Figure 5O:
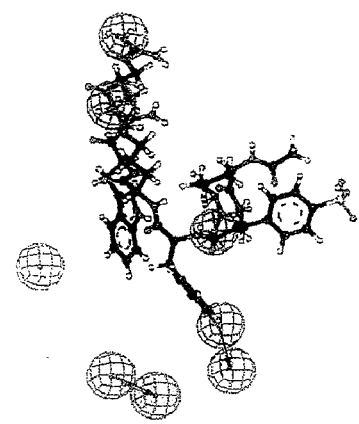
Figure 5P:
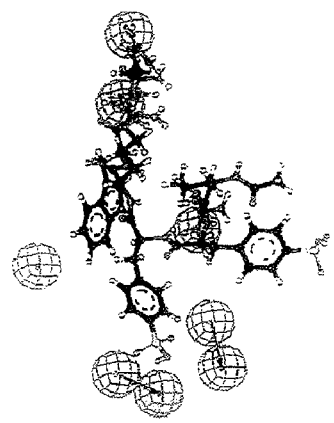
Figure 5Q:
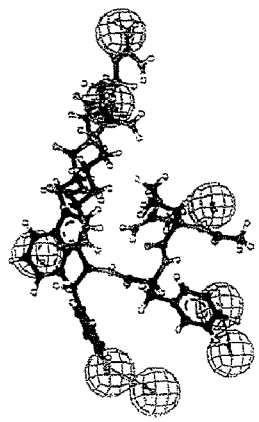
Figure 5R:
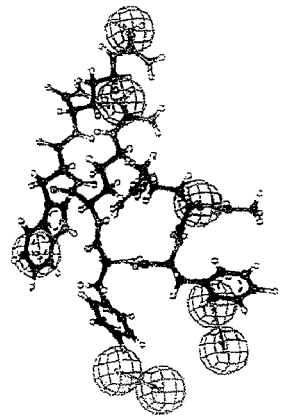
Figure 5S:
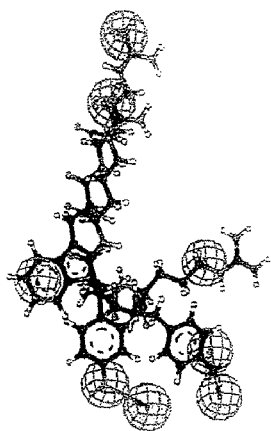
Figure 5T:
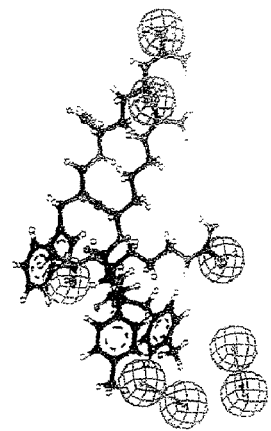
Figure 5U:
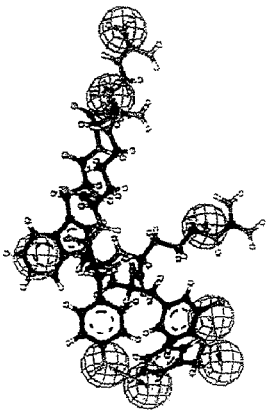
Figure 5V:
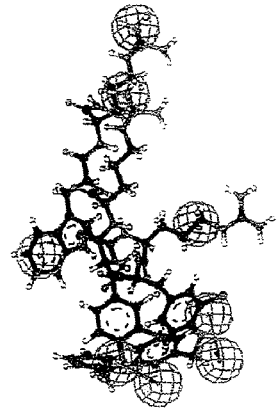
Figure 5W:
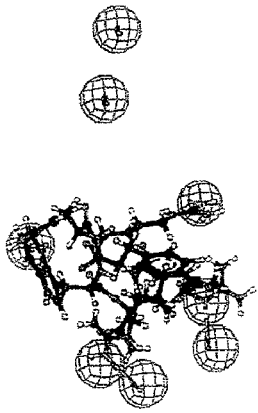
Figure 6A:
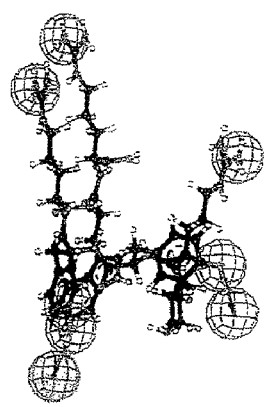
FIGS. 6A-6W compare the predicted structure of a group of peptide analogs of the invention in comparison with the pharmacophore hypothesis for IV-17-C (SEQ ID NO: 25)
Figure 6B:
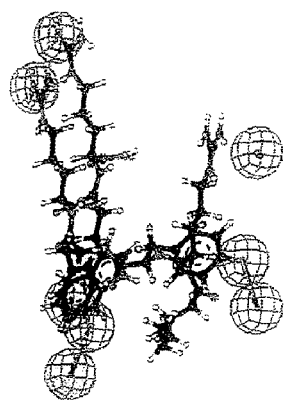
Figure 6C:
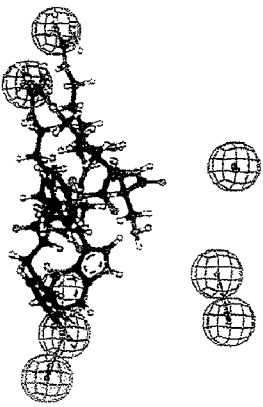
Figure 6D:
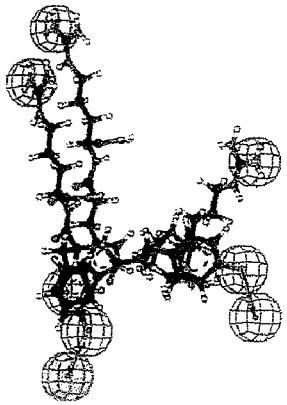
Figure 6E:
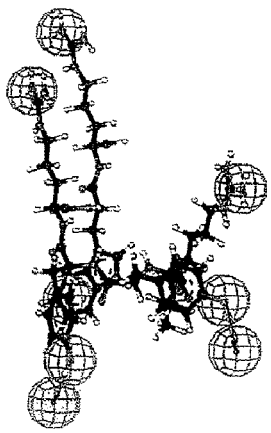
Figure 6F:
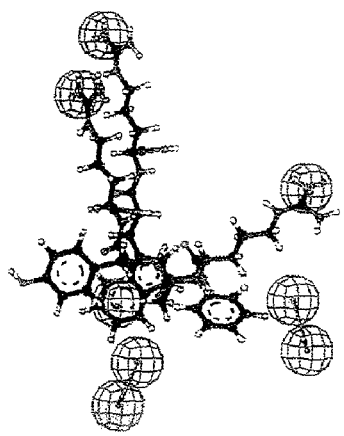
Figure 6G:
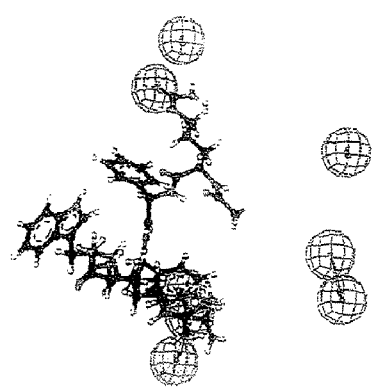
Figure 6H:
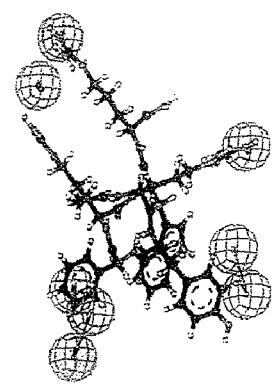
Figure 6I:
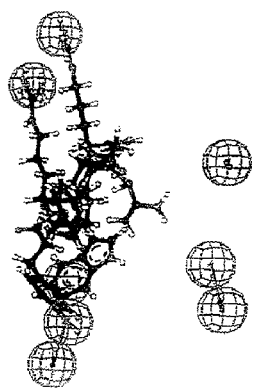
Figure 6J:
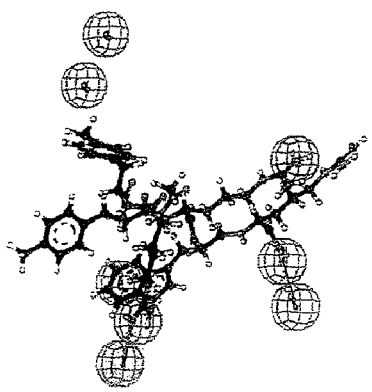
Figure 6K:
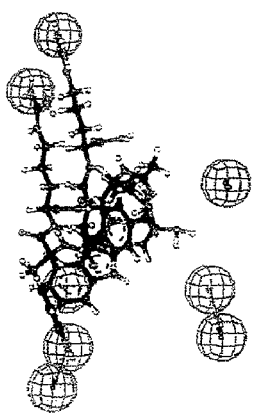
Figure 6L:
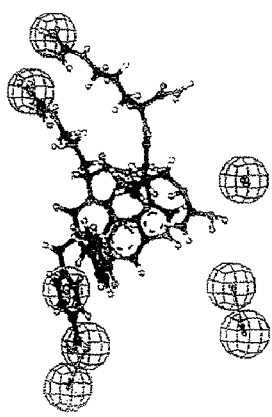
Figure 6M:
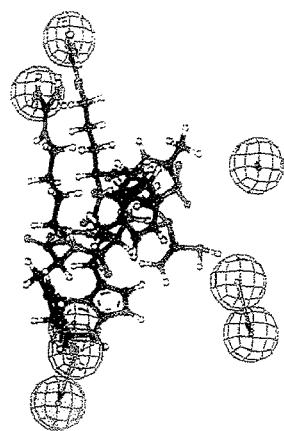
Figure 6N:
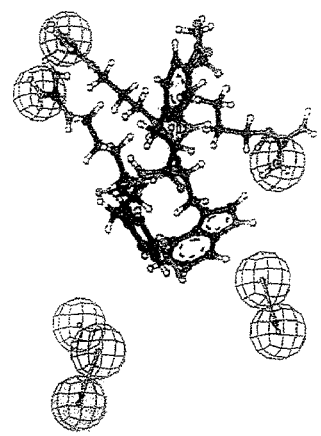
Figure 6O:
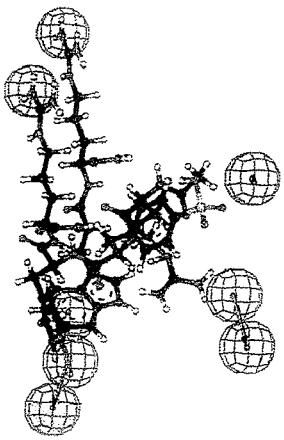
Figure 6P:
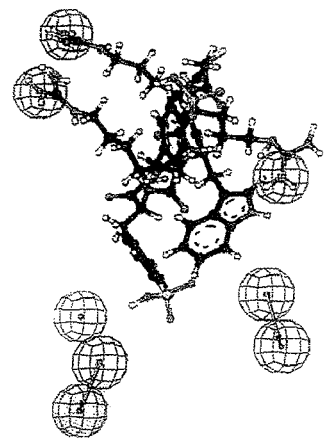
Figure 6Q:
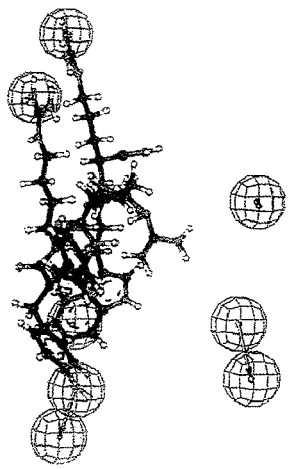
Figure 6R:
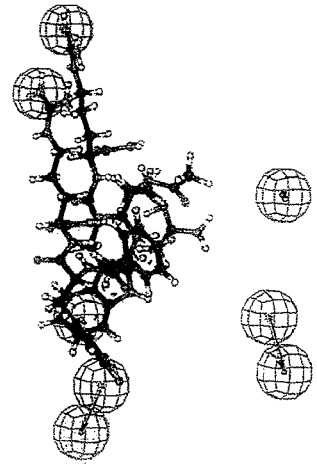
Figure 6S:
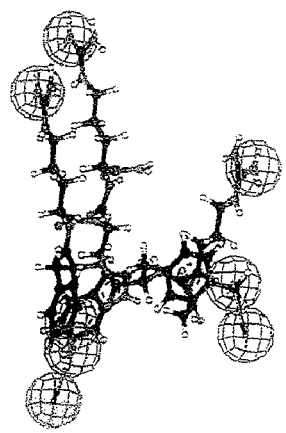
Figure 6T:
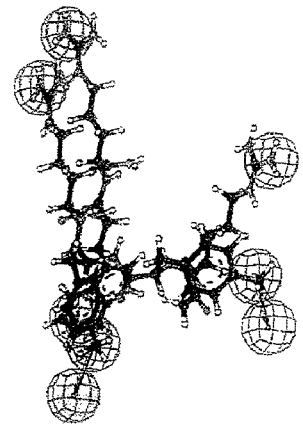
Figure 6U:
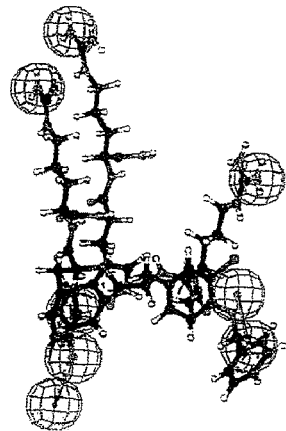
Figure 6V:
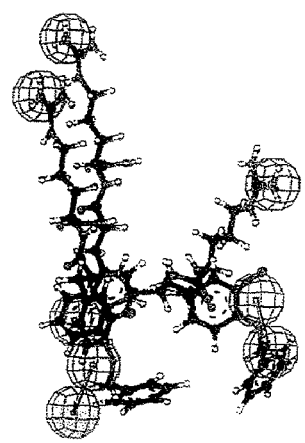
Figure 6W:
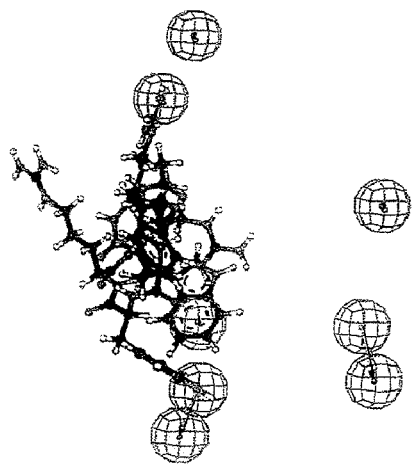
Figure 7A:
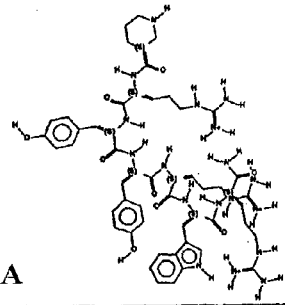
FIGS. 7A-7W show the 2-dimensional structures of a group of peptides of the invention.
Figure 7B:
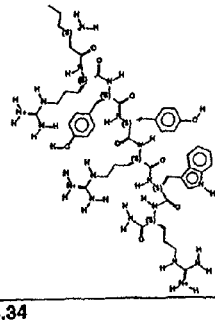
Figure 7C:
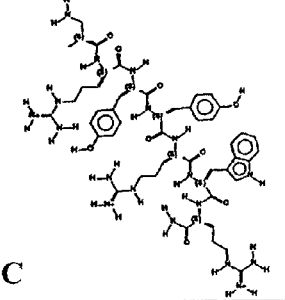
Figure 7D:
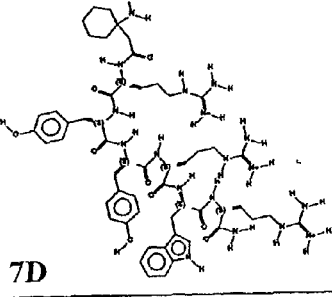
Figure 7E:
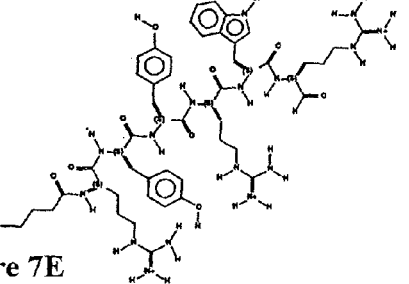
Figure 7F:
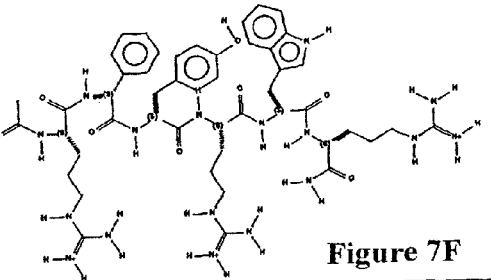

These molecules were subjected to computational analysis to predict their potential utility. The molecules were designed and modeled in CATALYST in "view compound workbench" mode. As a reference, the 3-dimensional structure of the compounds IV-16-C (SEQ ID NO: 24) and IV-17-C (SEQ ID NO: 25) are shown overlapped with their predicted 3-dimensional pharmacophores in FIGS. 4A and 4B, respectively. The structures of the newly-generated analogs were compared with these two pharmacophores, using the "compare fit" function of CATALYST. FIGS. 5A through 5W show the results of overlapping the predicted 3-dimensional structures of the hexapeptide analogs with the predicted pharmacophore of IV-16-C (SEQ ID NO: 24). Similarly, FIGS. 6A through 6W show the results of overlapping the predicted 3-dimensional structures of the hexapeptide analogs with the predicted pharmacophore of IV-17-C (SEQ ID NO: 25). FIGS. 7A through 7W show the simple 2-dimensional structures of each of the hexapeptide analog compounds investigated.

The results of the computational studies are shown in Table 4. In this table, the structures of the analog hexapeptides were compared with the pharmacophores using the "compare fit" function of CATALYST. Using these methods, best fit values ranging from 2.26 to 5.99 were obtained, the higher values indicating a better overlap of the pharmacophore "Hypothesis" and the analog and the lower values indicating a worse overlap. For example, value of zero indicates no overlap while a value of six indicates a perfect overlap.

TABLE 4

Results of Computational Experiments on Peptide Analogs

| Compound Name | Conformational Energy (KCal/mol) | Best Fit IV-16-C Hypothesis | Best Fit IV-17-C Hypothesis |
|---|---|---|---|
| VII-1-A | 81.23 | 4.91 | 5.99 |
| VII-2-A | 78.87 | 4.82 | 5.99 |
| VII-3-A | 82.51 | 3.82 | 3.95 |
| VII-4-B | 81.22 | 4.66 | 5.98 |
| VII-7-B | 78.17 | 4.92 | 5.97 |
| VII-9-A | 86.01 | 3.98 | 3.97 |
| VII-11-B | 85.13 | 3 | 2.75 |
| VII-13-B | 78.32 | 3.96 | 2.99 |
| VII-15-B | 145.90 | 3.25 | 3.79 |
| VII-17-B | 81.00 | 2.26 | 2.92 |
| VII-19-B | 204.71 | 3.82 | 3.96 |
| VII-21-C | 207.12 | 2.97 | 2.98 |
| VII-23-B | 205.06 | 3.77 | 3.97 |
| VII-25 | 150.5 | 2.99 | 2.98 |
| VII-27-B | 144.71 | 3.73 | 3.92 |
| VII-29-B | 146.01 | 2.98 | 2.99 |
| VII-31-B | 145.33 | 3.27 | 3.94 |
| VII-33-B | 145.02 | 3.00 | 3.00 |
| VII-35-C | 81.22 | 3.98 | 5 |
| VII-37-B | 81.28 | 3.00 | 3.99 |
| VII-39-D | 95.10 | 3.98 | 4.98 |
| VII-41 | 107.13 | 2.99 | 3.99 |
| VII-43-C | 75.53 | 3.18 | 2.99 |

Receptor binding studies were conducted on human ORL1 (opiate receptor like 1) transfected into Chinese hamster ovary (CHO) cells using each of the hexapeptide analog compounds of Table 3. All the compounds were evaluated for binding affinities. The results are shown in Table 5. Affinity was determined using [$^3$H] nociceptin binding to membranes derived from CHO cells transfected with human ORL-1. IC$_{50}$ values and Hill coefficients were then determined using the curve fitting program Prism, and Ki values were calculated from the formula Ki=IC$_{50}$/(1+L/Kd) (Chang and Prusoff), where Kd is the binding affinity of [$^3$H]nociceptin and L is the concentration of [$^3$H]nociceptin in each particular experiment. [L] of nociceptin was approximately 0.2 nM, and the Kd, as determined by the Scatchard analysis is 0.05 nM. The data shown in Table 5 represents the average ±SEM of at least two experiments conducted in triplicate.

ORL1-containing CHO cells were produced using cDNA obtained from Dr. Brigitte Kieffer. The cells are grown in Dulbeccols Modified Eagle Medium (DMEM) with 10% fetal bovine serum, in the presence of 0.4 mg/ml G418 and 0.1% penicillin/streptomycin, in 100-mm plastic culture dishes. For binding assays, the cells are scraped off the plate at confluence. For determination of inhibition of cAMP accumulation, cells are subcultured onto 24-well plates and used at confluence.

Receptor binding assays will be examined as described previously in Toll, 1992. Cells are removed from the plates by scraping with a rubber policeman, and then homogenized in Tris buffer using a Polytron homogenizer. Following this homogenization step, the cellular mixture is centrifuged once and washed by an additional centrifugation at 40,000×g for 15 min. The pellet formed during the centrifugation is resuspended in 50 mM Tris, pH 7.5. The resulting suspension is incubated with [$^3$H]nociceptin in a total volume of 1.0 ml, in a 96-well format, for 120 min at 25° C. Samples of the suspension are then filtered over glass fiber filters using a Wallac cell harvester.

For the ORL-1 binding experiments, 1 mg/ml bovine serum albumin is used to prevent absorption of the ligand to the glass tubes, and filters are soaked in 0.1% polyethyleneimine (PEI) to prevent adsorption to the glass fiber filters, thus lowering nonspecific binding considerably.

TABLE 5

Binding Affinities of Novel Peptide Analogs at ORL1

| Compound | $K_i$ (nM) ± SEM | Hill Coefficient |
|---|---|---|
| Nociceptin | 0.04 ± 0.005 | 1.0 |
| VII-1-A | 30.3 ± 2.9 | 0.97 |
| VII-2-A | 11.8 ± 1.9 | 1.0 |
| VII-3-A | 1.18 ± 0.18 | 0.72 |
| VII-4-B | 9.25 ± 2.05 | 1.0 |
| VII-7-B | 0.16 ± 0.05 | 0.8 |
| VII-11-B | 30.4 ± 3.62 | 0.93 |
| VII-13-B | 27.0 ± 3.85 | 0.73 |
| VII-15-B | 0.48 ± 0.18 | 0.79 |
| VII-17-B | 10.05 ± 1.44 | 1.06 |
| VII-19-B | 40.6 ± 15.9 | 1.0 |
| VII-21-C | >10,000 | |
| VII-23-B | 0.44 ± 0.26 | 0.74 |
| VII-27-B | 155 ± 15.2 | 1.12 |
| VII-29-B | >10,000 | |
| VII-31-B | 0.52 ± 0.13 | 0.81 |
| VII-33-C | 1.51 ± 0.005 | 0.89 |
| VII-35-C | 0.43 ± 0.05 | 0.75 |
| VII-37-B | 6.29 ± 0.15 | 0.82 |
| VII-39-D | 0.03 ± 0.02 | 1.03 |
| VII-43-C | 0.15 ± 0.02 | 0.73 |
| VII-49-B | 5.49 ± 0.0073 | 0.94 |
| VII-51-A | 0.3 ± 0.1333 | 0.7 |
| VII-53-B | 29.09 ± 0.0014 | 0.86 |
| VII-55-A | 39 ± 0.001 | 1.12 |
| VII-57-C | 41.93 ± 0.001 | 0.95 |
| VII-61-B | 0.05 ± 0.8 | 1.05 |
| VII-63-B | 0.17 ± 0.2353 | 1.01 |
| VII-65-F | 28.1 ± 0.0014 | 1.1 |
| VII-67-A | 5.59 ± 0.0072 | 1.07 |
| VII-71-B | 0.63 ± 0.0635 | 0.88 |
| VII-73-A | 0.04 ± 1 | 0.95 |
| VII-75-B | 26.69 ± 0.0015 | 0.75 |
| VII-77-A | 0.88 ± 0.0455 | 0.62 |
| VII-79-A | 2.54 ± 0.0157 | 0.89 |
| VII-87-B | 0.26± | |

For the data in Table 5, binding was conducted as described above. $IC_{50}$ values and Hill coefficients were determined using the curve-fitting program Prism. Ki values were calculated using the equation $Ki=IC_{50}/(1+[L]/Kd)$. [L] of nociceptin was approximately 0.2 nM, and the Kd, as determined by Scatchard analysis, was 0.05 nM. The data in Table 5 represent the average ±SEM of at least two experiments conducted in triplicate.

Table 6 shows the results of [$^{35}$S]GTPγS binding assays conducted using the compounds of Table 3. [$^{35}$S]GTPγS binding is conducted generally according to the methods described by Traynor and Nahorski (1995). First, cells are scraped from their tissue culture dishes into 20 mM HEPES, 1 mM EDTA. This suspension is then centrifuged at 500×g for 10 minutes. Following this, the cells were re-suspended in buffer and homogenized using a Polytron Homogenizer. The resulting homogenate was centrifuged at 20,000×g for 20 minutes. The pellet produced during centrifugation is next re-suspended in a buffer containing 20 mM HEPES, 10 mM $MgCl_2$, and 100 mM NaCl, having a pH of 7.4. The suspension is re-centrifuged at 20,000×g and then suspended once more in the buffer outlined above. The pellet may be frozen at −70° C. prior to the final centrifugation. For the binding assay, membranes (10-20 μg protein) are incubated with [$^{35}$S]GTPγS (50 μM), GDP (usually 10 μM), and the desired compound, in a total volume of 1 ml, for 60 minutes at 25° C. Samples are filtered over glass fiber filters and counted as described for the binding assays. A dose response with the full agonist nociceptin was then conducted in each experiment to identify full and partial agonist compounds.

TABLE 6

Stimulation of [$^{35}$S]GTPγS Binding of Peptide Analogs in CHO Cell Membranes Transfected with ORL1

| Compound | $EC_{50}$ (nM) ± SEM | % Stimulation ± SEM |
|---|---|---|
| Nociceptin | 0.5 ± 0.001 | 100 |
| VII-1-A | FLAT | <20 |
| VII-2-A | FLAT | <20 |
| VII-3-A | 68 ± 0 | 29.1 ± 1.9 |
| VII-4-B | FLAT | <20 |
| VII-7-B | FLAT | <20 |
| VII-15-B | 18.8 ± 0.5 | 59.8 ± 16.2 |
| VII-17-B | FLAT | <20 |
| VII-19-B | 854 ± 29.7 | 45.5 ± 8 |
| VII-23-B | 15.7 ± 0.6 | 56.6 ± 20.4 |
| VII-31-B | 35.7 ± 0.2 | 54.4 ± 1.2 |
| VII-33-C | FLAT | <20 |
| VII-35-C | 51.1 ± 11.6 | 52.1 ± 0.6 |
| VII-37-B | FLAT | <20 |
| VII-39-D | 0.3 ± 0.08 | 89 ± 7.1 |
| VII-43-C | 29.5 ± 8.0 | 49.7 ± 6.6 |
| VII-49-B | FLAT | <20 |
| VII-51-A | 156.1 ± 64.39 | 49.1 ± 0.19 |
| VII-53-B | 167.3 ± 103.73 | 39.5 ± 4 |
| VII-55-A | 1230.8 ± 1007.25 | 26.6 ± 1.95 |
| VII-57-C | 358 ± 5.15 | 37.4 ± 2.64 |
| VII-61-B | 2 ± 0.26 | 70.4 ± 1.98 |
| VII-63-B | 3.2 ± 0.65 | 43.2 ± 0.59 |
| VII-65-F | FLAT | 13.7 ± 1.175 |
| VII-67-A | FLAT | <20 |
| VII-71-B | 7.5 ± 0.0 | 33.65 ± 16.83 |
| VII-73-A | 5.2 ± 0.24 | 52.7 ± 0.175 |
| VII-75-B | FLAT | <20 |
| VII-77-A | 115.1 ± 55.055 | 19 ± 6.92 |
| VII-79-A | FLAT | <20 |
| VII-87-B | 3.9 | 72 |

In these [$^{35}$S]GTPγS assays, binding was conducted as described above. $EC_{50}$ values and percent stimulation were determined using the program Prism. The data shown represent the average ±SEM of at least two experiments conducted in triplicate. If percent stimulation was less than 20%, $EC_{50}$ values could not be reliably determined, and the compound was considered an antagonist.

As seen in Table 5, the structural modifications made in peptide analogs have produced a variety of receptor affinities, potencies, and efficacies. The highest affinity compound (VII-39-D) (SEQ ID NO: 7) has a Ki value of 0.03 nM, equivalent to that of nociceptin. The modifications also produced compounds ranging from a full agonist (VII-39-D) (SEQ ID NO: 7), to several antagonists. The activity of several of these compounds is compared in FIG. 8.

Figure 8:
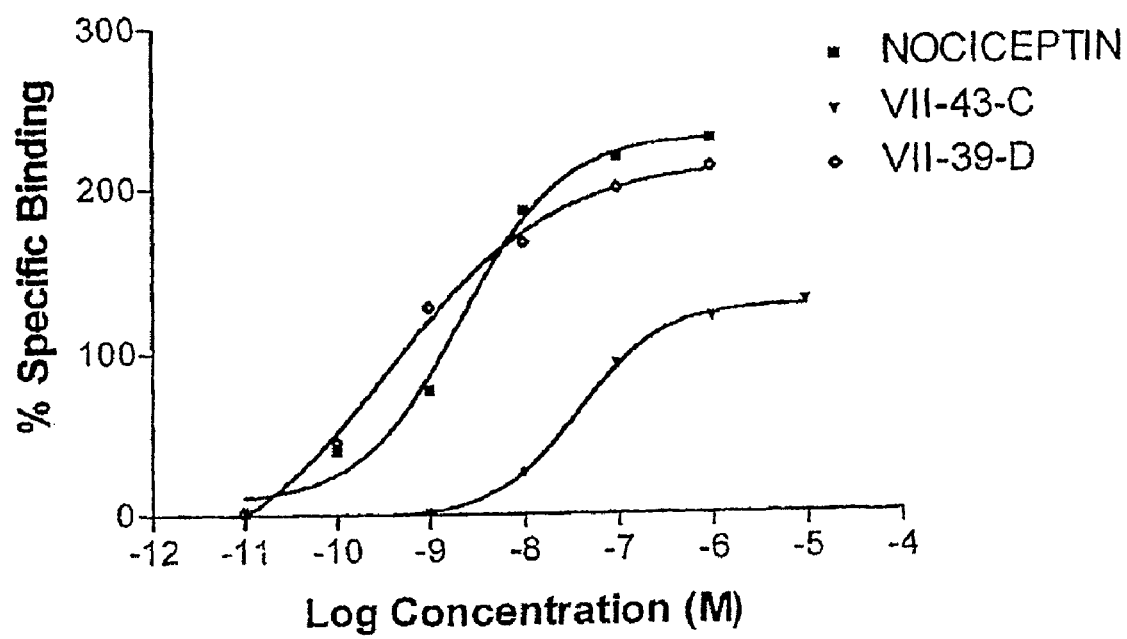
FIG. 8 is a chart showing the agonist activity of VII-39-D and the partial agonist activity of VII-43-C observed in a nociceptin-induced [$^{35}$S]GTPγS binding assay.
Figure 9:
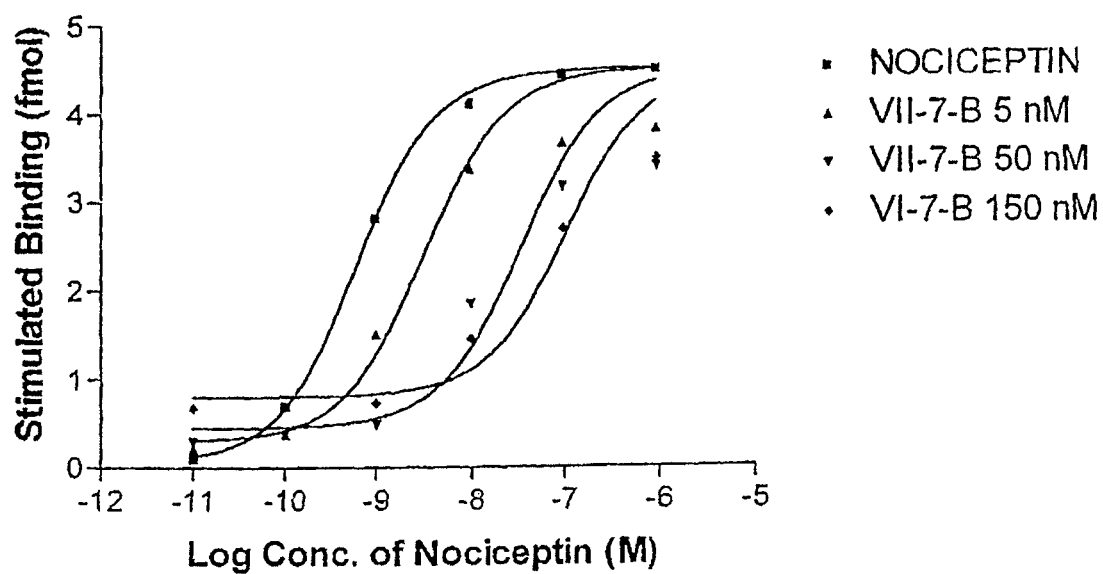
FIG. 9 is a chart showing the antagonist activity of VII-7-B of right-shifting the dose/response curve for nociceptin stimulation of [$^{35}$S]GTPγS binding.
Figure 10:
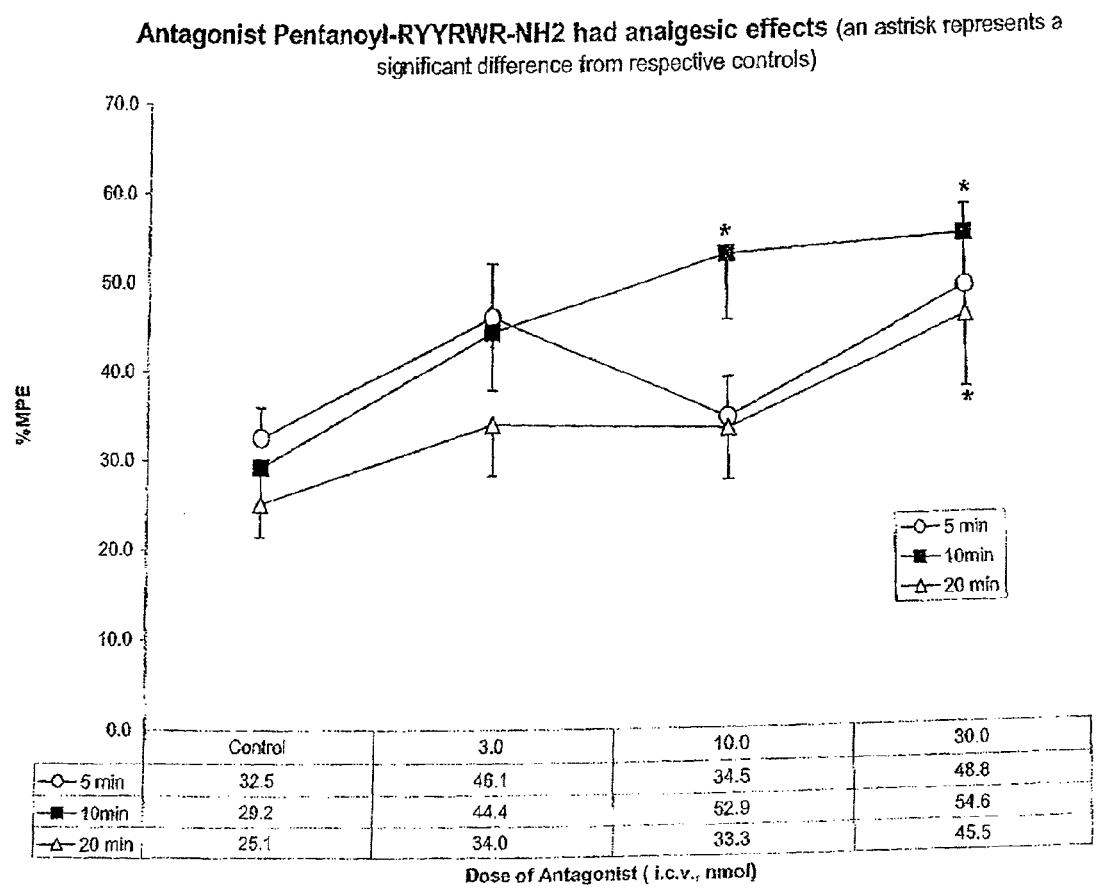
FIG. 10 is a chart showing the analgesic effects of the antagonist Pentanoyl-RYYRWRNH$_2$ (SEQ ID NO: 26)

Specifically, FIG. 8 shows stimulation of [$^{35}$S]GTPγS binding by the full agonist VII-39-D (SEQ ID NO: 7), the partial agonist VII-43-C (SEQ ID NO: 6), and the full agonist, standard nociceptin. As can be seen in Table 5 and FIG. 8, VII-39-D (SEQ ID NO: 7) also has potency similar to that of nociceptin. The most potent antagonist VII-7-B (SEQ ID NO: 26) has been tested for antagonist potency by Schild analysis. As seen in FIG. 9, VII-7-B (SEQ ID NO: 26) produces a dose-dependent parallel shift in the nociceptin dose response curve. This indicates competitive inhibition. Schild analysis produced the following values: Ke=1.06±0.11, slope=−1.02 (competitive inhibition), $pA_2$=8.99±0.05. This compound is more potent as an antagonist when tested in vitro than any antagonist found in the literature to date.

As briefly discussed above, peptide analog VII-39-D (SEQ ID NO: 7) is a very potent agonist. An additional hexapeptide analog VII-87-B (SEQ ID NO: 23) was similarly tested and shown to be an agonist. Agonists have been shown to have efficacy as anxiolytics against some forms of chronic pain when administered intrathecally. VII-7-B (SEQ ID NO: 26) is a very potent antagonist. Some such antagonists have been shown to be effective in animal thermal pain models, particularly when administered into the brain.

EXAMPLES

The above hexapeptide drugs were used in in vivo experimentation to show their potential medical usefulness. Specifically, the antagonist VII-7-B (SEQ ID NO: 26), the agonist 87-B (SEQ ID NO: 23), and the agonist VII-39-D (SEQ ID NO: 7) were tested in vivo alone or in combination with morphine. The antagonist VII-7-B (SEQ ID NO: 26) was also tested in combination with morphine and N/OFQ.

Nociception was assessed using a tail flick assay with mice kept on a 12-hours light and 12-hours dark regimen and housed 10 per cage. Tail flick latencies were determined using a Tail Flick Analgesia Instrument (Stoelting) that uses radiant heat. This instrument is equipped with an automatic quantification of tail flick latency and a 15-second cutoff to prevent damage to the animal's tail. During testing, the focused beam of light was applied to the lower half of the animal's tail, and tail flick latency was recorded. Baseline values for tail flick latency were determined before drug administration in each animal. Basal tail flick latency was between 3.7 and 6.3 seconds (average 4.6±0.1 SEM). Immediately after testing, animals were lightly anaesthetized with isoflurane and received a unilateral 2 µl intracerebroventricular injection approximately 2.0 mm caudal and approximately 2.0 mm lateral with respect to the bregma (the junction of the sagittal and coronal sutures of the skull), and 3 mm ventral from the skull surface). Injections may be made using a Hamilton syringe equipped with a 26-guage needle fitted with a plastic sleeve to prevent more than 2.5 mm penetration beyond the skull surface. Following the intracerebroventricular injections, the animals were tested for tail flick latencies at 5-, 10-, and 20-minutes post-injection.

Antinociception was quantified by the following formula:

% Antinociception=100*[(test latency−baseline latency)/(15−baseline latency)]. If the animal subject did not respond prior to the 15-second cutoff, the animal was assigned a score of 100%.

Behavioral results were analyzed using ANOVAs with the antagonist, agonist, morphine, and N/OFQ as between group variables and post-drug treatment time (5-, 10-, and 20-minutes) as the repeated measure followed by Dunnet post-hoc tests where appropriate. The level of significance was set at $p<0.05$.

In the experiments examining the combined effects of morphine alone or with the antagonist and/or N/OFQ, planned comparisons were used to compare the effects of combined administration of antagonist/N/OFQ and morphine to the morphine alone groups at the three different post-infusion time points since it was hypothesized that the antagonist and/or N/OFQ would alter morphine-induced analgesia. Also, planned comparisons were used to compare the groups that received N/OFQ and morphine since it was hypothesized that the antagonist would decrease the efficiency of N/OFQ on morphine-induced analgesia. The modified Boniferroni Test was used for these planned comparisons (p value was set at $P<0.036$). Doses were determined based on the potency of the compounds tested.

Example 1

In a first Example, the antagonist VII-7-B (SEQ ID NO: 26) having the sequence: Pentanoyl-RYYRWR-NH$_2$ was assayed for analgesic effects. In this assay, the responses of a control mouse were compared against mice receiving three different dosages of the VII-7-B antagonist (SEQ ID NO: 26). The responses were measured at 5, 10, and 20 minutes after the intracerebroventricular injection of antagonist. The test and baseline latencies were then used to calculate the antinociception as detailed above. In the figure, an asterisk represents a significant difference of a test animal from the respective controls. Here, the antagonist VII-7-B (SEQ ID NO: 26) showed analgesic properties in those mice receiving the 10.0 and 30.0 nmol intracerebroventricular injections at 10 and 20 minutes post-injection.

Example 2

The antagonist was next assayed for the ability to reverse the inhibition of morphine-induced analgesia. In this assay, the control received morphine alone, while test animals received morphine +3 nmol of the antagonist, morphine +10 nmol of the antagonist. These results were compared with test animals receiving morphine +3 nmol nociceptin, morphine +nociceptin +3 nmol antagonist, and morphine +nociceptin +10 nmol antagonist. For each of these animals, response was measured at 5, 10, and 20 minutes after intracerebroventricular injection.

Figure 11:
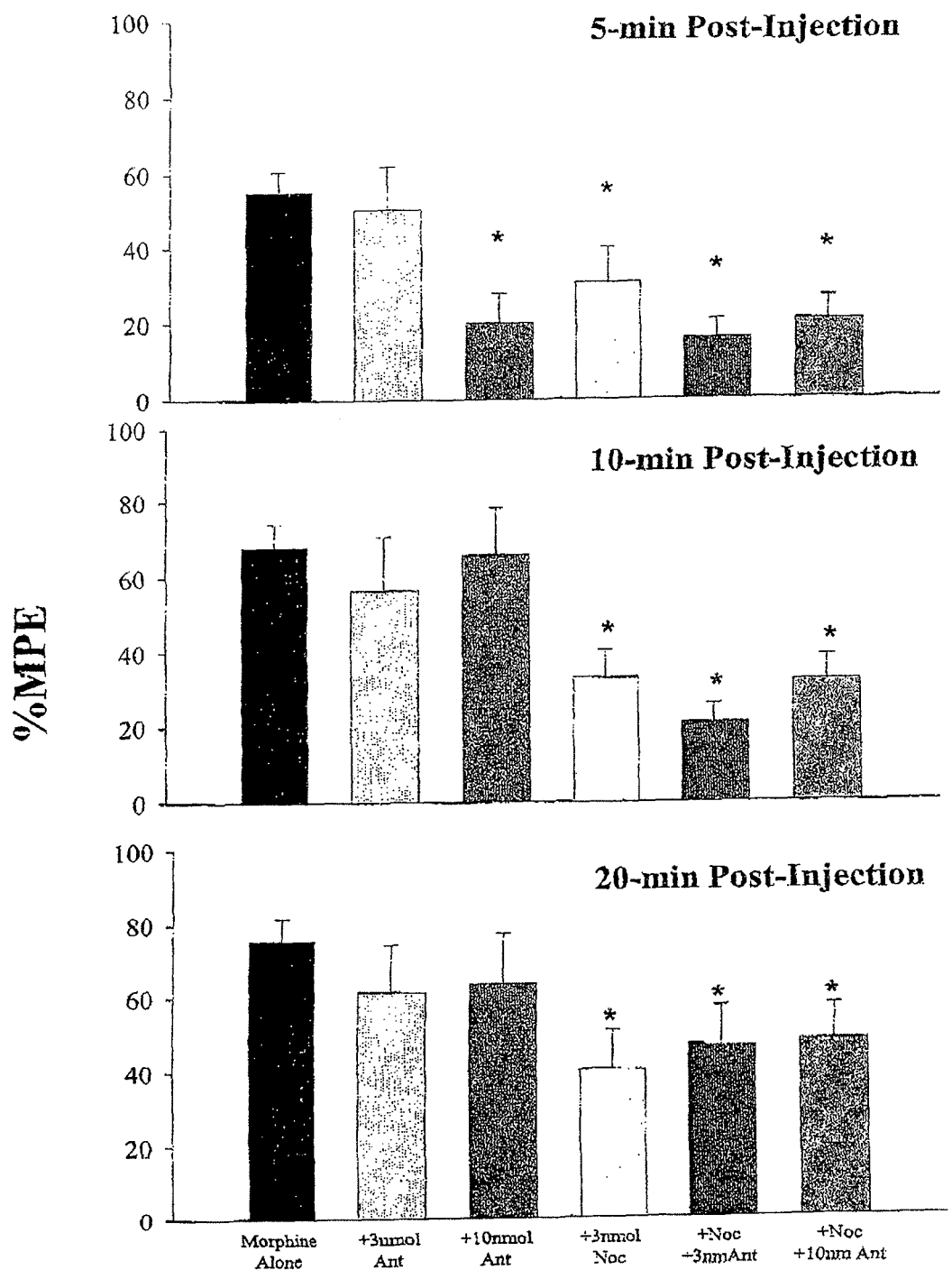
FIG. 11 is a set of charts showing that the Pentanoyl-RYYRWRNH$_2$ (SEQ ID NO: 26) antagonist did not reverse the inhibition of morphine-induced analgesia brought about by nociceptin.

As shown in FIG. 11, the antagonist did not appear to significantly reverse the inhibition of morphine-induced analgesia. Little reversal was observed in the two animals receiving morphine and antagonist. Some reversal appears to be present in the animals receiving morphine, antagonist, and nociceptin. This result was explored further.

Figure 12:
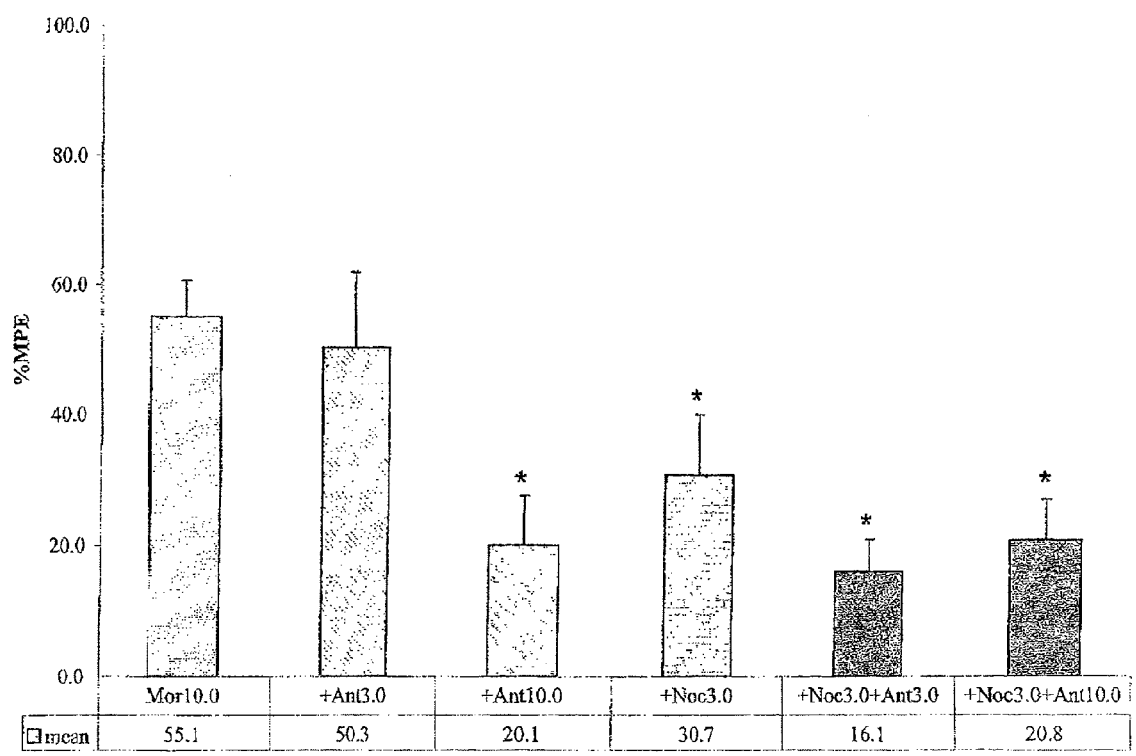
FIG. 12 is a chart showing the ability of the Pentanoyl-RYYRWRNH$_2$ (SEQ ID NO: 26) antagonist to reduce morphine-induced analgesia at 5 minutes post-injection.
Figure 13:
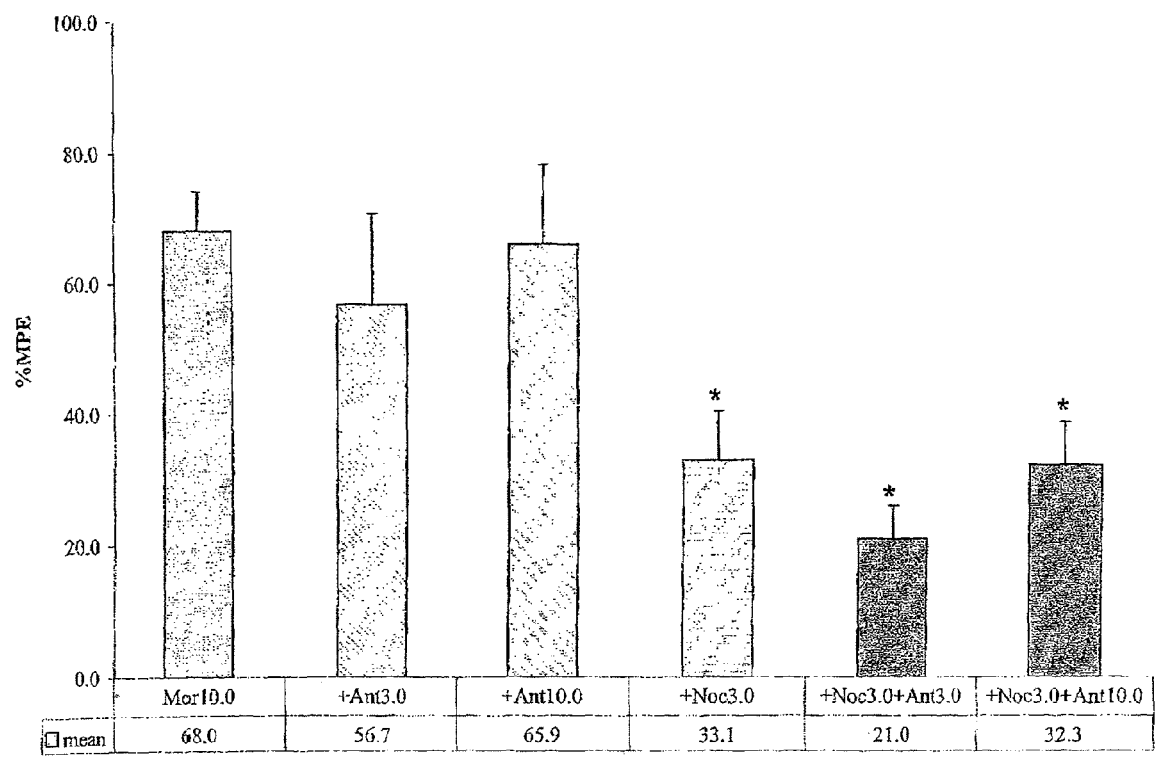
FIG. 13 is a chart showing the ability of the Pentanoyl-RYYRWRNH$_2$ (SEQ ID NO: 26) antagonist to reduce morphine-induced analgesia at 10 minutes post-injection.
Figure 14:
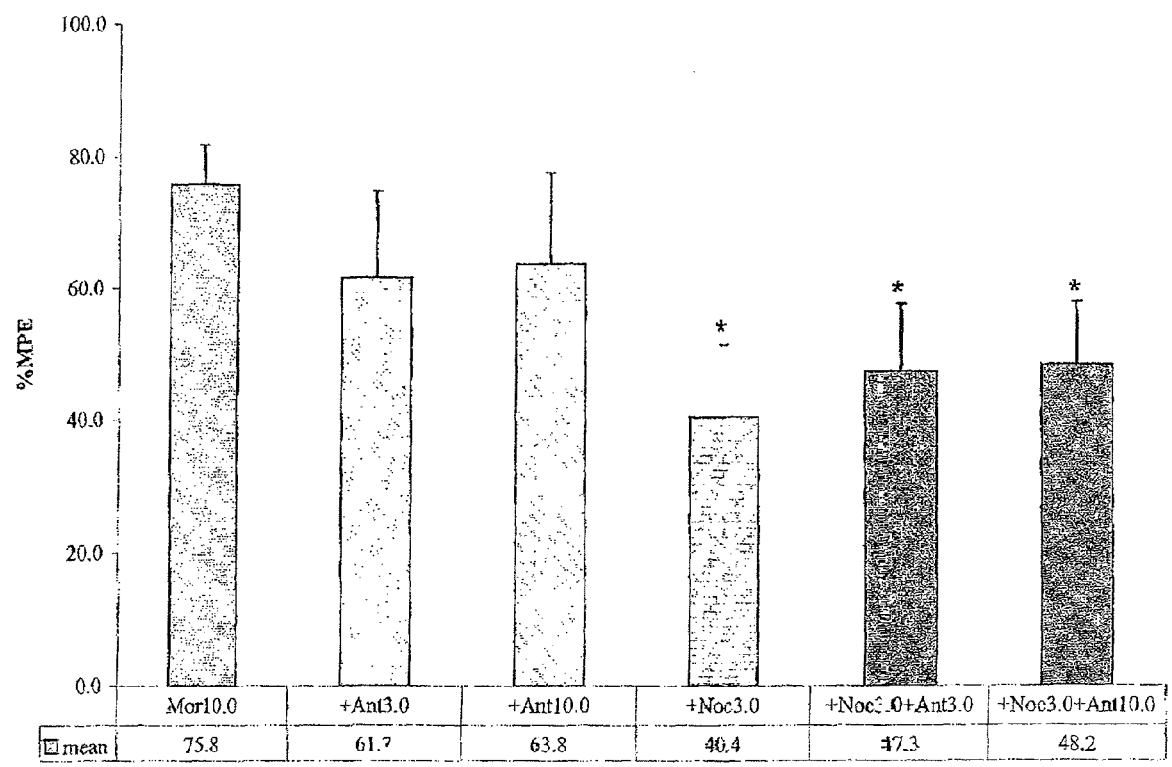
FIG. 14 is a chart showing the ability of the Pentanoyl-RYYRWRNH$_2$ (SEQ ID NO: 26) antagonist to reduce morphine-induced analgesia at 20 minutes post-injection.

Referring now to FIG. 12, at 5 minutes post-injection, the administration of 10 nmol of the VII-7-B (SEQ ID NO: 26) antagonist alone, as well as in combination with N/OFQ resulted in a reduction in morphine-induced analgesia. In this Figure, as above, asterisks represent a significant difference from morphine alone. As seen in FIGS. 13 and 14, however, at 10 and 20 minutes post injection, the antagonist did not alter the effects of nociceptin.

Example 3

Figure 15:
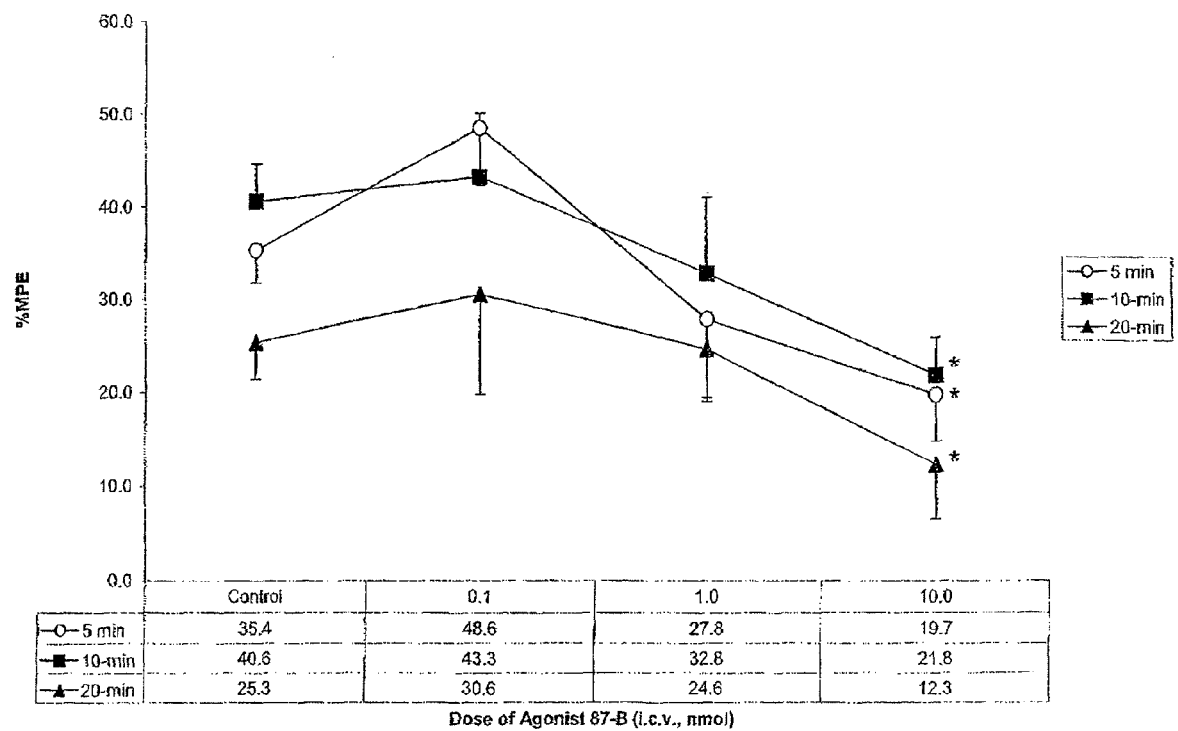
FIG. 15 is a chart showing the pro-nociceptive effects of the administration of the VII-87-B agonist (SEQ ID NO: 23)

The agonist 87-B was next assayed for analgesic effects. In this assay, the responses of a control mouse were compared against mice receiving three different dosages of the VII-87-B agonist (SEQ ID NO: 23). The responses were measured at 5, 10, and 20 minutes after the intracerebroventricular injection of agonist. The test and baseline latencies were then used to calculate the antinociception as detailed above. The results of this assay are shown in FIG. 15. In the figure, an asterisk represents a significant difference of a test animal from the respective controls.

Here, the agonist VII-87-B (SEQ ID NO: 23) induced pro-nociception in mice receiving 10 nmol of agonist by intracerebroventricular injection at 5, 10, and 20 minutes post-injection.

The agonist VII-87-B was further investigated by evaluating its ability to reverse morphine-induced analgesia. In this assay, the control animal received 10 nmols of morphine alone, while test animals received morphine +0.1 nmol of the agonist, morphine +1.0 nmol of the agonist, or morphine +10.0 nmol of the agonist. For each of these animals, response was measured at 5, 10, and 20 minutes after intracerebroventricular injection.

Figure 16:
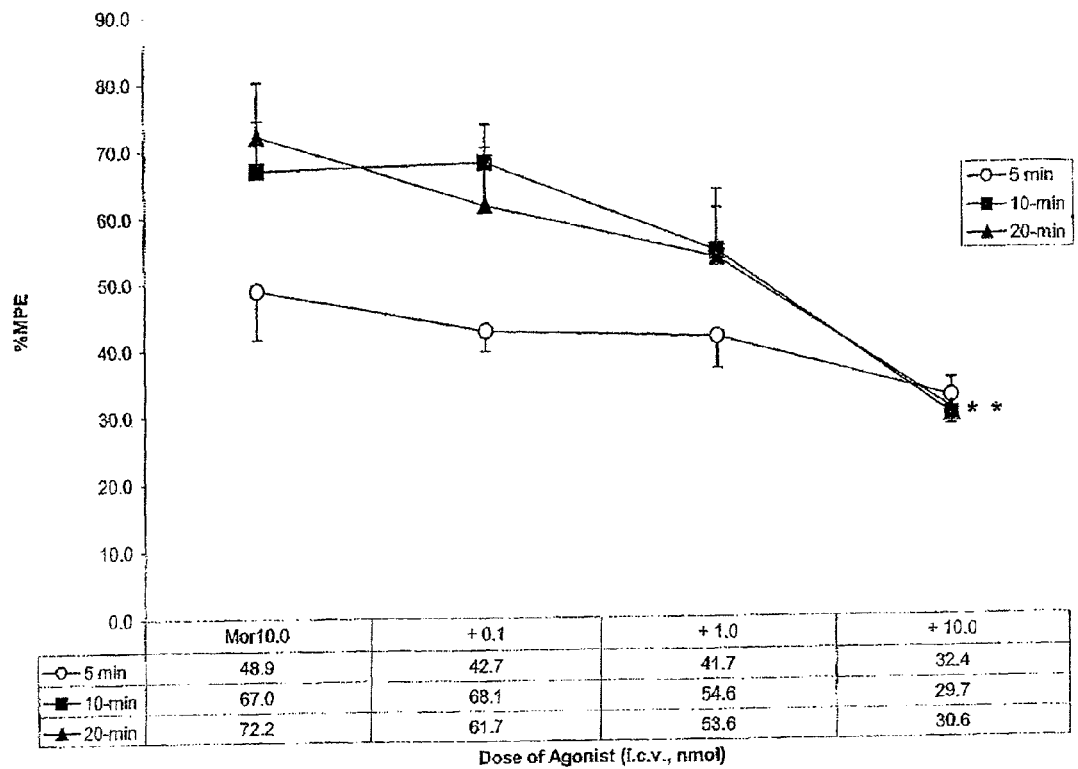
FIG. 16 is a chart showing the dose-dependent reversal of morphine-induced analgesia by administration of the agonist VII-87-B (SEQ ID NO: 23)

The results of this assay are shown in FIG. 16. This assay showed dose-dependent reversal of morphine-induced analgesia at 10 and 20 minutes by the antagonist in animals injected with 10 nmol of antagonist in addition to the morphine.

Example 4

Figure 17:
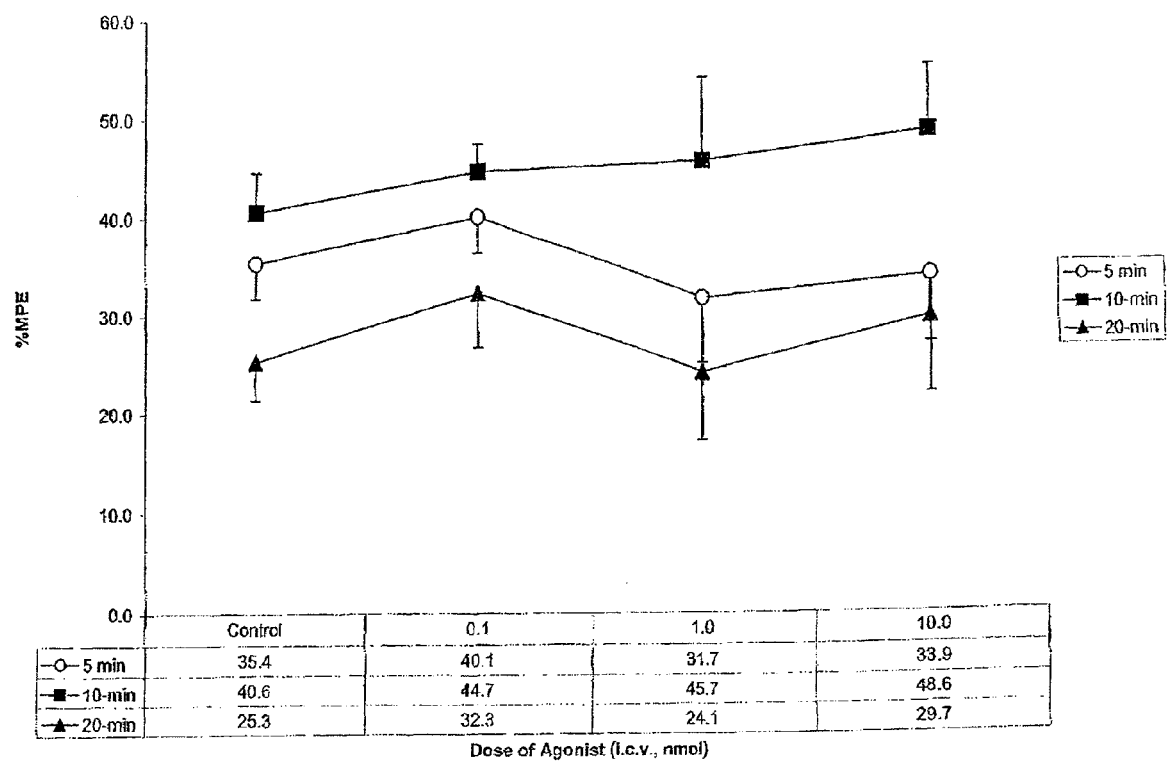
FIG. 17 is a chart showing the effects of the administration of the agonist VII-39-D (SEQ ID NO: 7)

The agonist 39-D was next assayed for analgesic effects. In this assay, the responses of a control mouse were compared against mice receiving three different dosages of the VII-39-D agonist (SEQ ID NO: 7). The responses were measured at 5, 10, and 20 minutes after the intracerebroventricular injection of agonist. The test and baseline latencies were then used to calculate the antinociception as detailed above. The results of this assay are shown in FIG. 17.

The agonist VII-39-D (SEQ ID NO: 7) did not induce anti- or pro-nociception in mice receiving 0.1, 1.0, or 10.0 nmol of agonist by intracerebroventricular injection at 5, 10, and 20 minutes post-injection.

Figure 18:
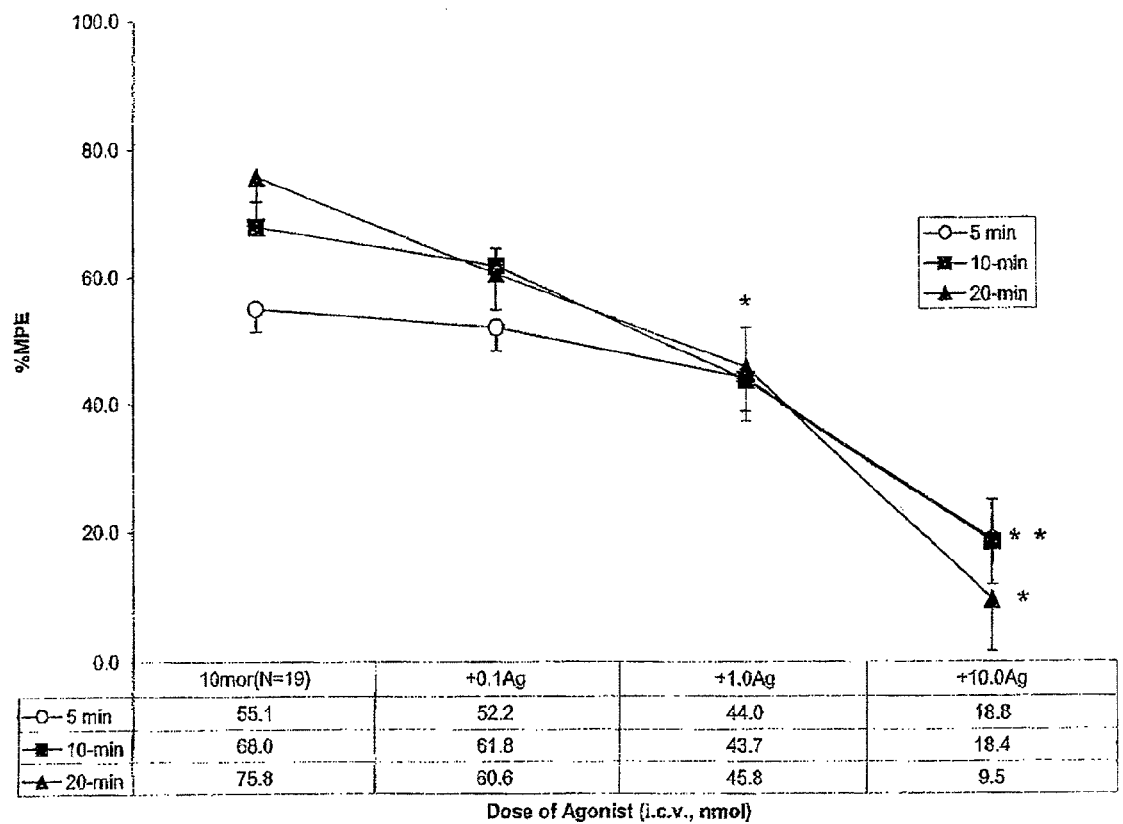
FIG. 18 is a chart showing the attenuation of morphine-induced analgesia by agonist VII-39-D (SEQ ID NO: 7).

The agonist VII-39-D was then further investigated by evaluating its ability to reverse morphine-induced analgesia. In this assay, the control animal received 10 nmols of morphine alone, while test animals received morphine +0.1 nmol of the agonist, morphine +1.0 nmol of the agonist, or morphine +10.0 nmol of the agonist. For each of these animals, response was measured at 5, 10, and 20 minutes after intracerebroventricular injection. The results of this assay are shown in FIG. 18. This assay showed attenuation of morphine-induced analgesia at 5, 10, and 20 minutes by the agonist in animals injected with 1.0 and 10 nmol of agonist in addition to the morphine.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed and desired to be secured by United States Letters Patent is:

1. A hexapeptide of the formula:
   Arg-Xaa-Tyr-Arg-Trp-Arg (SEQ ID NO: 17), wherein the hexapeptide binds with the ORL-1 receptor, wherein Xaa is selected from the group consisting of natural amino acids, D-amino acids, non-natural amino acids, and modified natural amino acids, the natural amino acids consisting of Gly, Ala, Val, Leu, Ile, Met, Pro, Phe, Trp, Ser, Thr, Asn, Gln, Cys, Lys, Arg, His, Asp, and Glu, the modified natural amino acids excluding Phe (4-Me), Phe (4-COOH), Phe (4-NO$_2$,), Phe (4-F), Phe (4-CN), Tyr (4-Me), Tyr (3-Cl), and Tyr (BN, 3-Cl), the hexapeptide having an amino terminus and a carboxy terminus, either or both of which may optionally be modified.

2. The hexapeptide of claim 1, having the formula of SEQ ID NO: 1.

3. The hexapeptide of claim 1, having the formula of SEQ ID NO: 2.

4. The hexapeptide of claim 1, having the formula of SEQ ID NO: 3.

5. The hexapeptide of claim 1, having the formula of SEQ ID NO: 4.

6. The hexapeptide of claim 1, having the formula of SEQ ID NO: 6.

7. The hexapeptide of claim 1, having the formula of SEQ ID NO: 5.

8. The hexapeptide of claim 1, having the formula of SEQ ID NO: 7.

9. The hexapeptide of claim 1, having the formula of SEQ ID NO: 23.

10. A hexapeptide of the formula:
    Arg-Tyr-Xaa-Arg-Trp-Arg (SEQ ID NO: 18), wherein the hexapeptide binds with the ORL-1 receptor, wherein Xaa is selected from the group consisting of natural amino acids, D-amino acids, non-natural amino acids, and modified natural amino acids, the natural amino acids consisting of Gly, Ala, Val, Leu, Ile, Met, Pro, Phe, Trp, Ser, Thr, Asn, Gln, Cys, Lys, Arg, His, Asp, and Glu, the hexapeptide having an amino terminus and a carboxy terminus, either or both of which may optionally be modified.

11. The hexapeptide of claim 10, having the formula of SEQ ID NO: 12.

12. The hexapeptide of claim 10, having the formula of SEQ ID NO: 13.

13. The hexapeptide of claim 10, having the formula of SEQ ID NO: 20.

14. The hexapeptide of claim 10, having the formula of SEQ ID NO: 21.

15. The hexapeptide of claim 10, having the formula of SEQ ID NO: 16.

16. The hexapeptide of claim 10, having the formula of SEQ ID NO: 22.

17. The hexapeptide of claim 10, wherein Xaa is a modified Tyr amino acid molecule.

18. The hexapeptide of claim 17, wherein Xaa is Tyr (2, 6 di-Me) (SEQ ID NO: 15).

19. A hexapeptide of the formula:
    Arg-Tyr-Tyr-Arg-Xaa-Arg (SEQ ID NO: 27), wherein the hexapeptide binds with the ORL-1 receptor, wherein Xaa is selected from the group consisting of natural amino acids, D-amino acids, non-natural amino acids, and modified natural amino acids, the natural amino acids consisting of Gly, Ala, Val, Leu, Met, Pro, Phe, Trp, Ser, Thr, Asn, Gln, Tyr, Cys, Lys, Arg, His, Asp, and Glu, the hexapeptide having an amino terminus and a carboxy terminus, either or both of which may optionally be modified.

* * * * *